(12) United States Patent
Carballada et al.

(10) Patent No.: US 9,877,910 B2
(45) Date of Patent: Jan. 30, 2018

(54) DEVICE FOR ACHIEVING LIFT AND VOLUME TO HAIR

(75) Inventors: Jose Antonio Carballada, Cincinnati, OH (US); Dana Hance Wolsing, Morning View, KY (US); James Lee Drobish, Wyoming, OH (US); Kazunori Nakasai, Shiga (JP); Shinji Nishimura, Shiga (JP)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 10/991,680

(22) Filed: Nov. 18, 2004

(65) Prior Publication Data

US 2005/0109359 A1    May 26, 2005

Related U.S. Application Data

(63) Continuation of application No. PCT/US03/37759, filed on Nov. 21, 2003.

(51) Int. Cl.
| | |
|---|---|
| *A45D 24/22* | (2006.01) |
| *A61K 8/81* | (2006.01) |
| *A45D 1/04* | (2006.01) |
| *A45D 1/18* | (2006.01) |
| *A45D 8/12* | (2006.01) |
| *A45D 20/00* | (2006.01) |
| *A45D 24/16* | (2006.01) |
| *A61K 8/73* | (2006.01) |
| *A61K 8/87* | (2006.01) |
| *A61Q 5/06* | (2006.01) |

(52) U.S. Cl.
CPC ............ *A61K 8/817* (2013.01); *A45D 1/04* (2013.01); *A45D 1/18* (2013.01); *A45D 8/12* (2013.01); *A45D 20/00* (2013.01); *A45D 24/16* (2013.01); *A61K 8/736* (2013.01); *A61K 8/8158* (2013.01); *A61K 8/8182* (2013.01); *A61K 8/87* (2013.01); *A61Q 5/06* (2013.01); *A61K 2800/594* (2013.01)

(58) Field of Classification Search
CPC ... A45D 1/04; A45D 1/18; A45D 8/12; A45D 20/00; A45D 24/16
USPC ....... 132/118, 224, 225, 227, 228, 231, 232, 132/236, 272, 112–116
See application file for complete search history.

(56) References Cited

U.S. PATENT DOCUMENTS

| | | | | |
|---|---|---|---|---|
| 3,721,250 A | * | 3/1973 | Walter et al. | 132/112 |
| 3,760,821 A | * | 9/1973 | Weddington | 132/118 |
| 3,805,811 A | * | 4/1974 | Dorn | 132/228 |
| 3,854,489 A | * | 12/1974 | Doyle et al. | 132/112 |
| 3,935,423 A | * | 1/1976 | Pucci | 219/225 |

(Continued)

FOREIGN PATENT DOCUMENTS

| | | |
|---|---|---|
| CN | 1328796 A | 1/2002 |
| WO | WO-98/07345 A1 | 2/1998 |

(Continued)

*Primary Examiner* — Rachel Steitz
(74) *Attorney, Agent, or Firm* — Linda M. Sivik

(57) ABSTRACT

The present invention is directed to a hair styling device for providing lift to a mass of undifferentiated hair stands on a scalp region comprising: a bundling means for gathering hair strands into hair bundles; a reservoir, in fluid communication with the bundling means, comprising a styling composition; and a means to hold and further align the hair strands along and beyond the bundling means.

21 Claims, 28 Drawing Sheets

(56) References Cited

U.S. PATENT DOCUMENTS

| | | | |
|---|---|---|---|
| 4,503,317 A | | 3/1985 | Mancillas |
| 4,702,265 A | * | 10/1987 | Weddington .................. 132/118 |
| 5,091,630 A | * | 2/1992 | Djuric .......................... 219/222 |
| 5,223,694 A | * | 6/1993 | Tsuji et al. .................... 219/225 |
| 5,553,632 A | * | 9/1996 | Burkhardt ..................... 132/271 |
| 5,621,980 A | * | 4/1997 | Kingsbury ........................ 34/97 |
| 5,738,121 A | * | 4/1998 | Westerveld et al. .......... 132/113 |
| 5,857,470 A | | 1/1999 | Schmidt |
| 6,119,702 A | * | 9/2000 | Habibi .......................... 132/224 |
| 6,199,558 B1 | | 3/2001 | Schmidt |
| 6,325,072 B1 | | 12/2001 | Smetana |
| 6,752,157 B2 | * | 6/2004 | Lu Shao Hua ............... 132/109 |
| 6,895,975 B2 | * | 5/2005 | Hafemann .................... 132/228 |
| 2002/0153020 A1 | * | 10/2002 | Fiore ............................ 132/114 |
| 2004/0000319 A1 | * | 1/2004 | Carballada et al. .......... 132/224 |
| 2006/0021629 A1 | * | 2/2006 | Mu et al. ...................... 132/116 |

FOREIGN PATENT DOCUMENTS

| | | |
|---|---|---|
| WO | WO-99/13843 A1 | 3/1999 |
| WO | WO-99/45814 A1 | 9/1999 |
| WO | WO-03/077702 A2 | 9/2003 |

\* cited by examiner

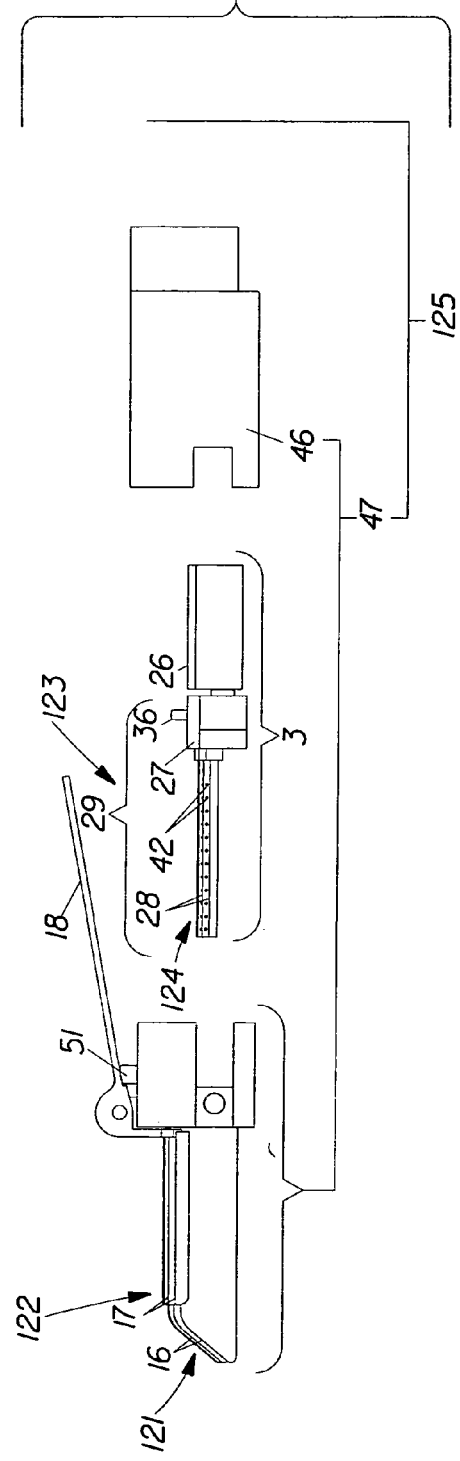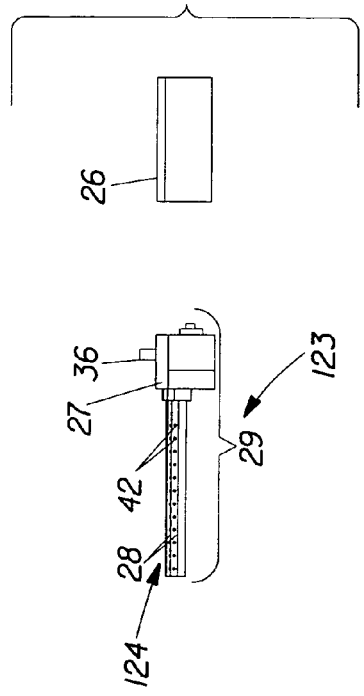

| P | Plug | D | Diode |
| S | Plug | M | Motor |
| F | Plug | Th | Thermostant |
| R | Plug | H | Heater |

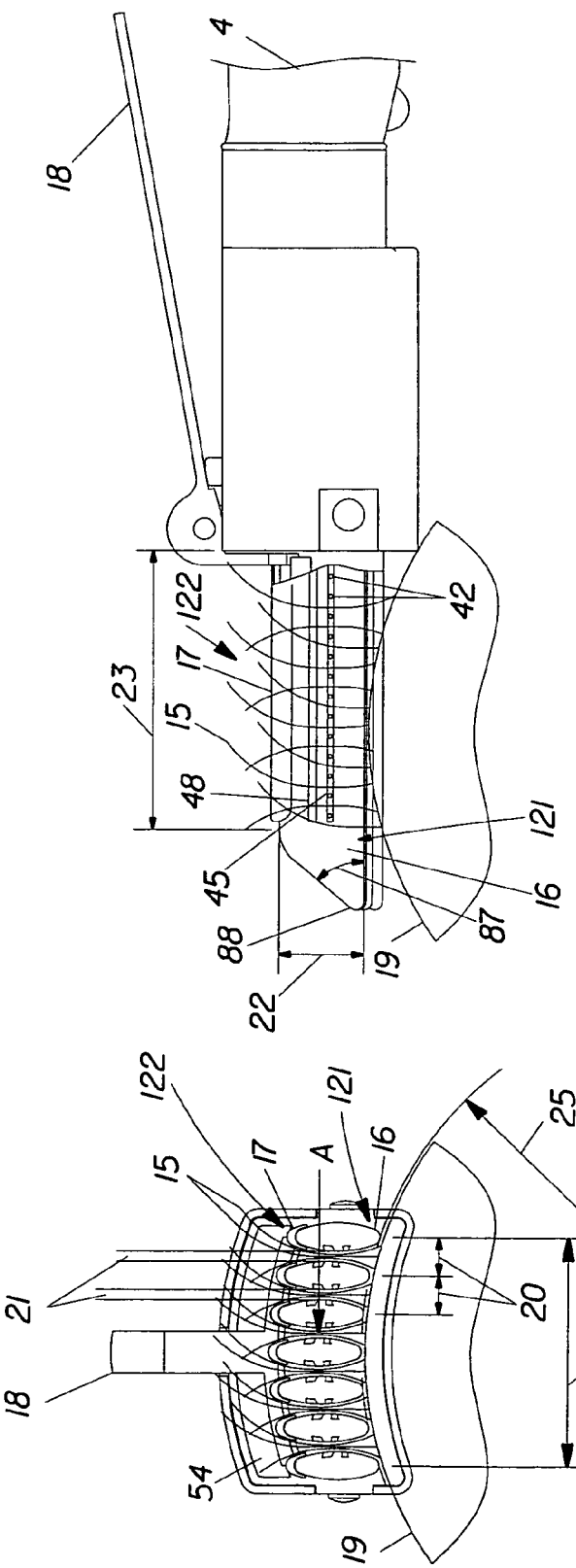

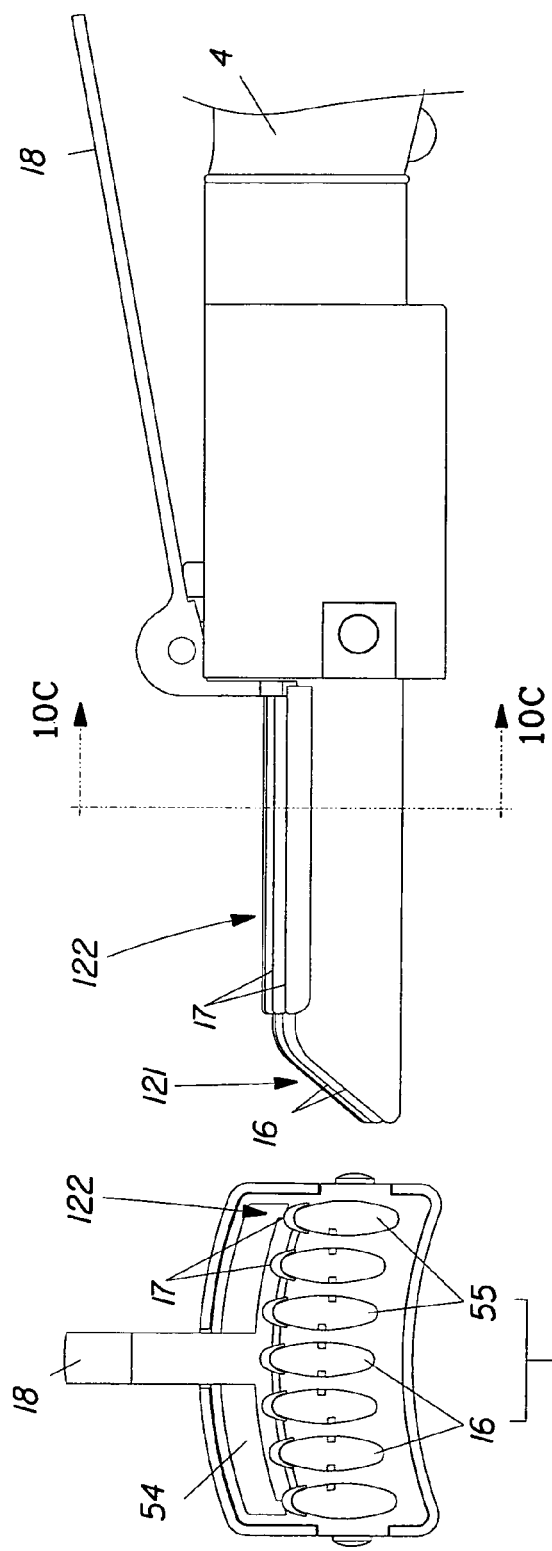

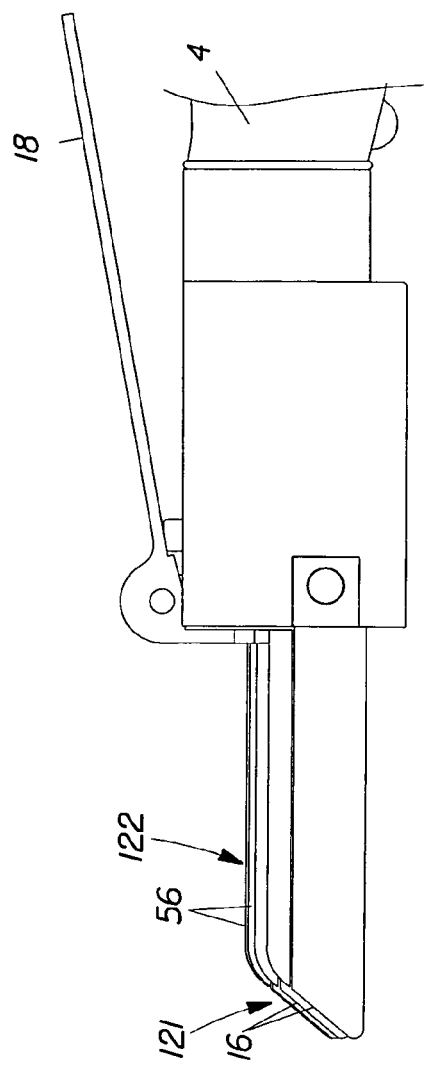
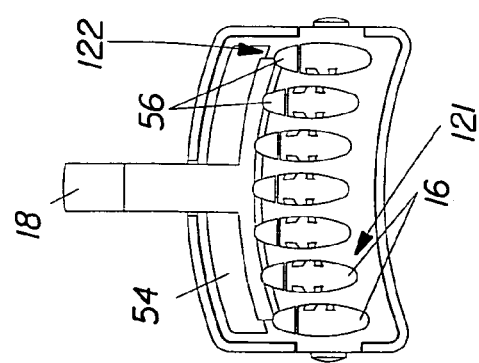
Fig. 11A
Fig. 11B

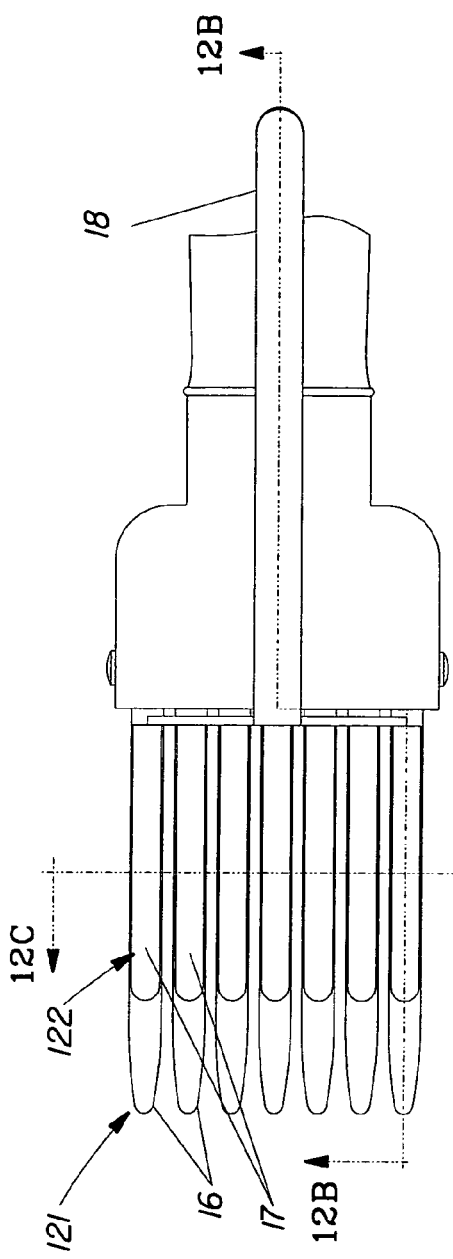
Fig. 12A
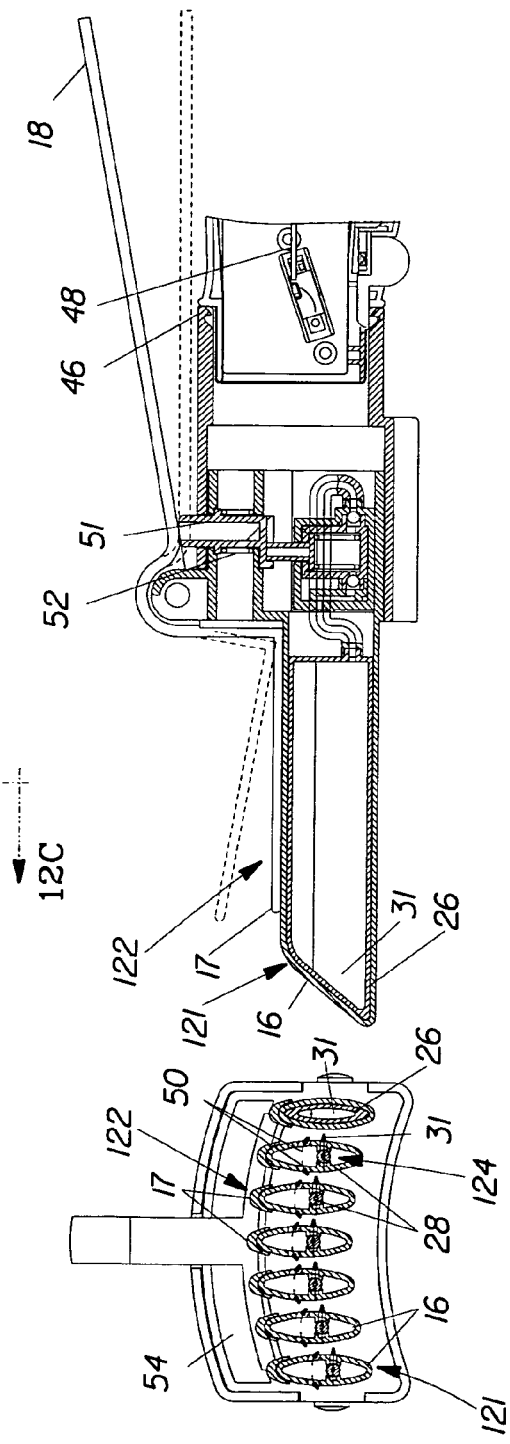
Fig. 12B
Fig. 12C

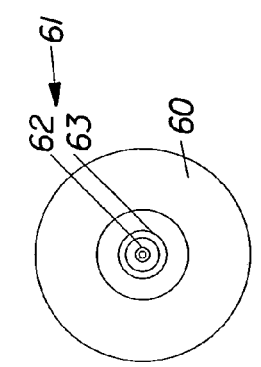
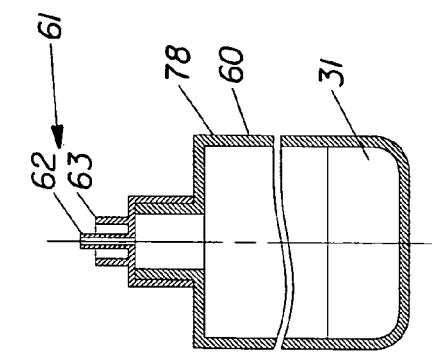
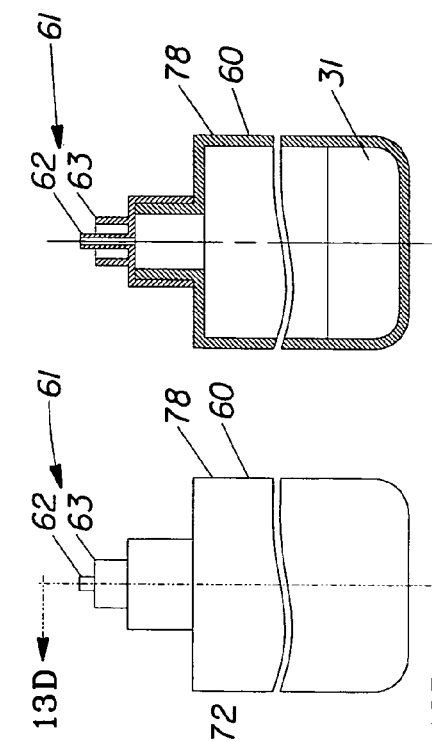
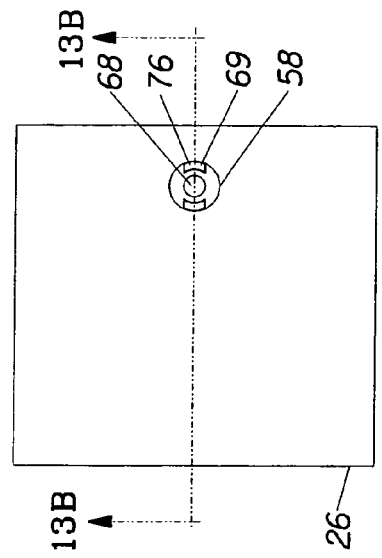
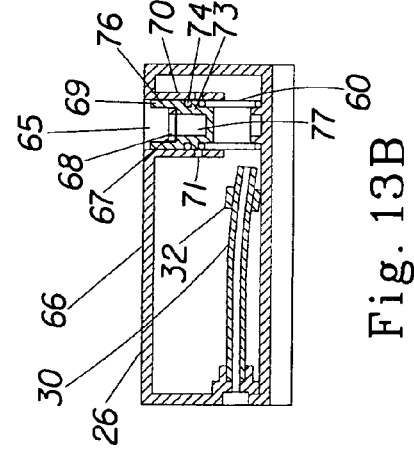
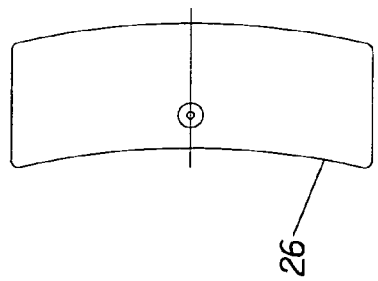

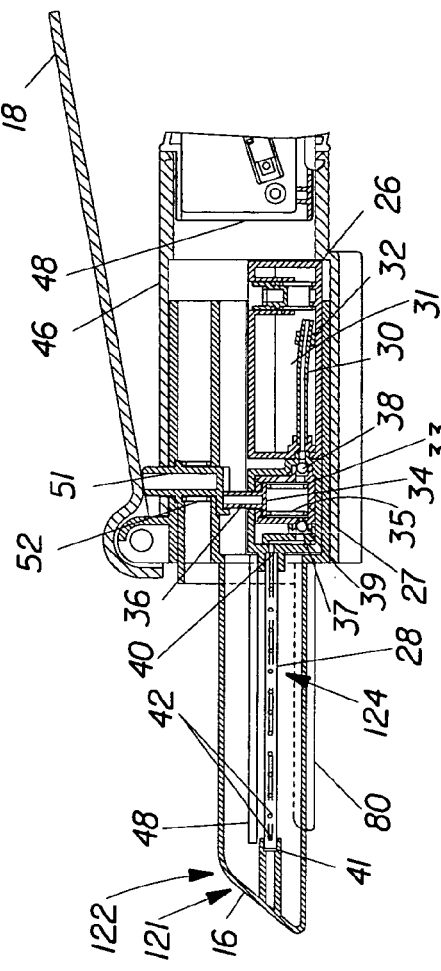
Fig. 14A
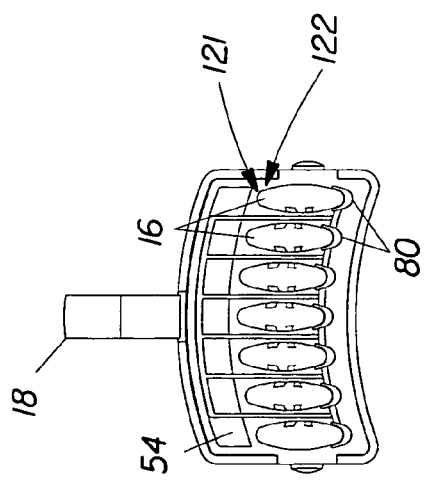
Fig. 14B
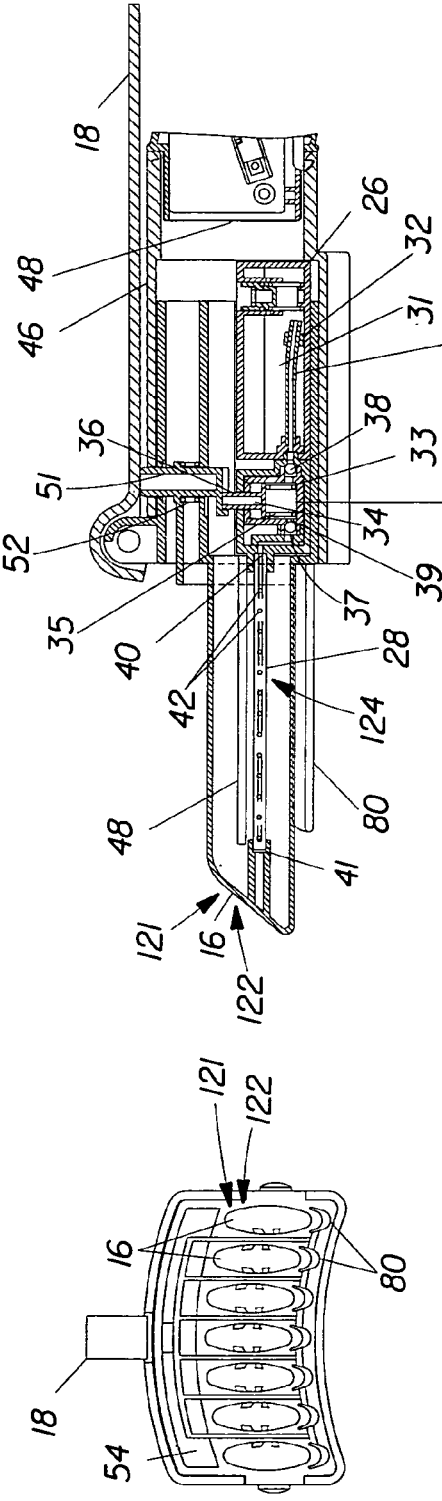
Fig. 14C
Fig. 14D

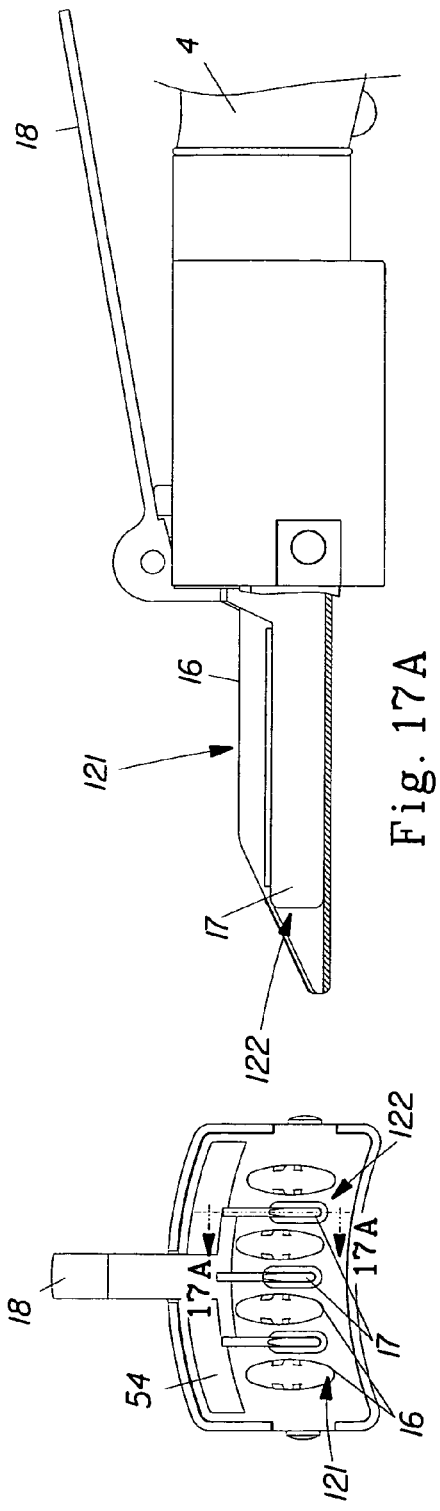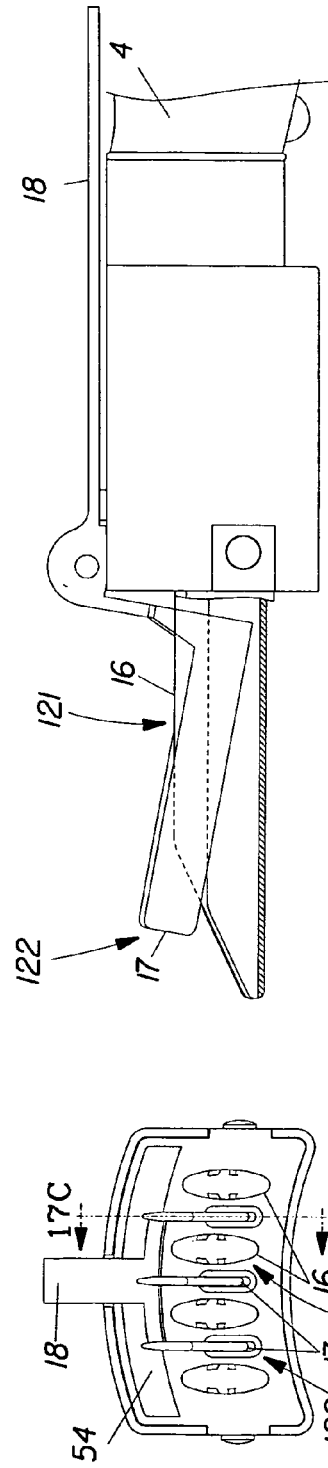
Fig. 17A Fig. 17B Fig. 17C Fig. 17D

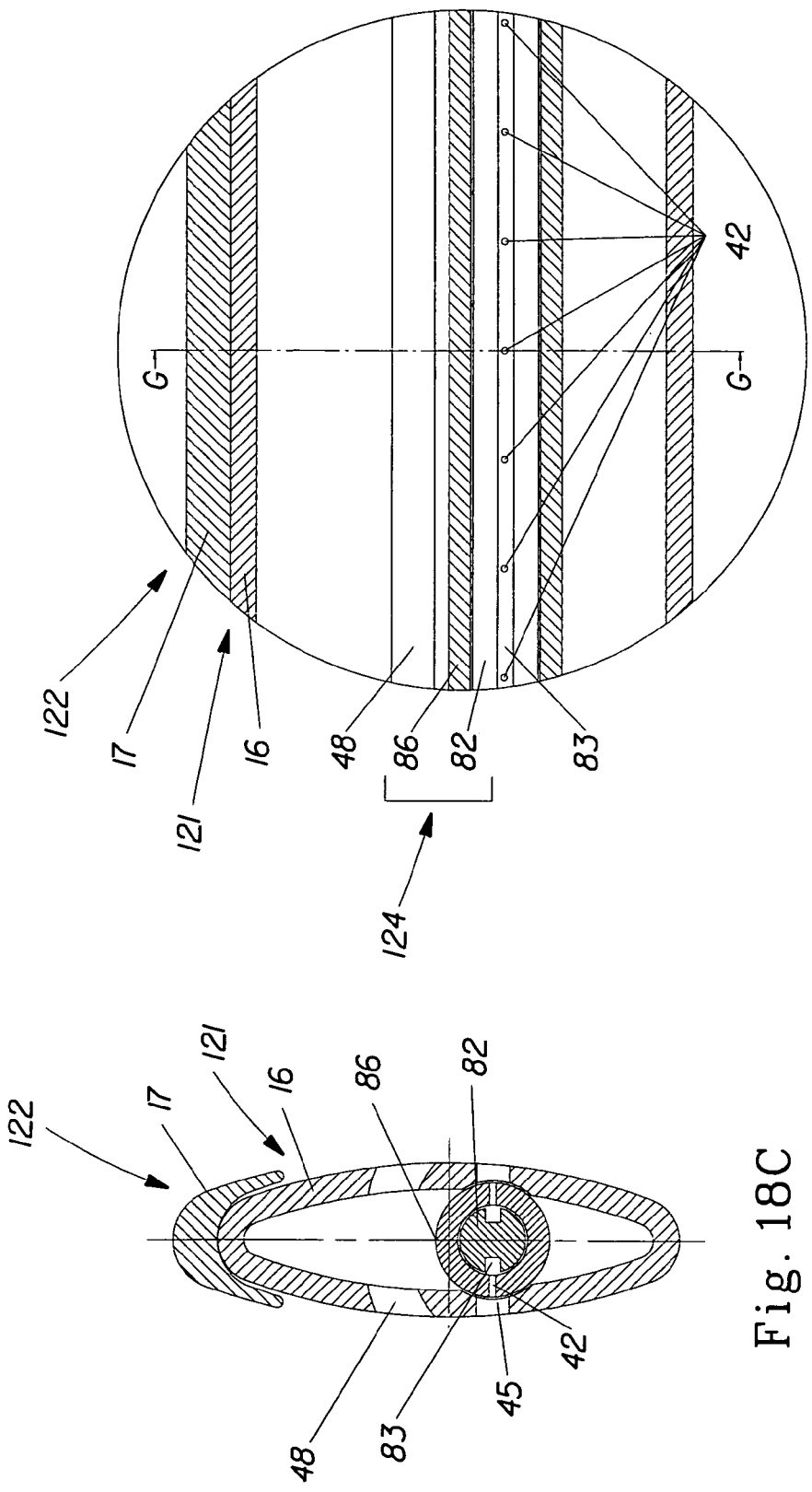

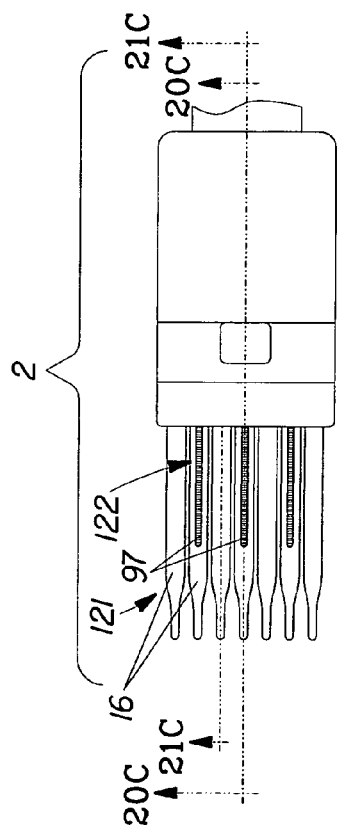
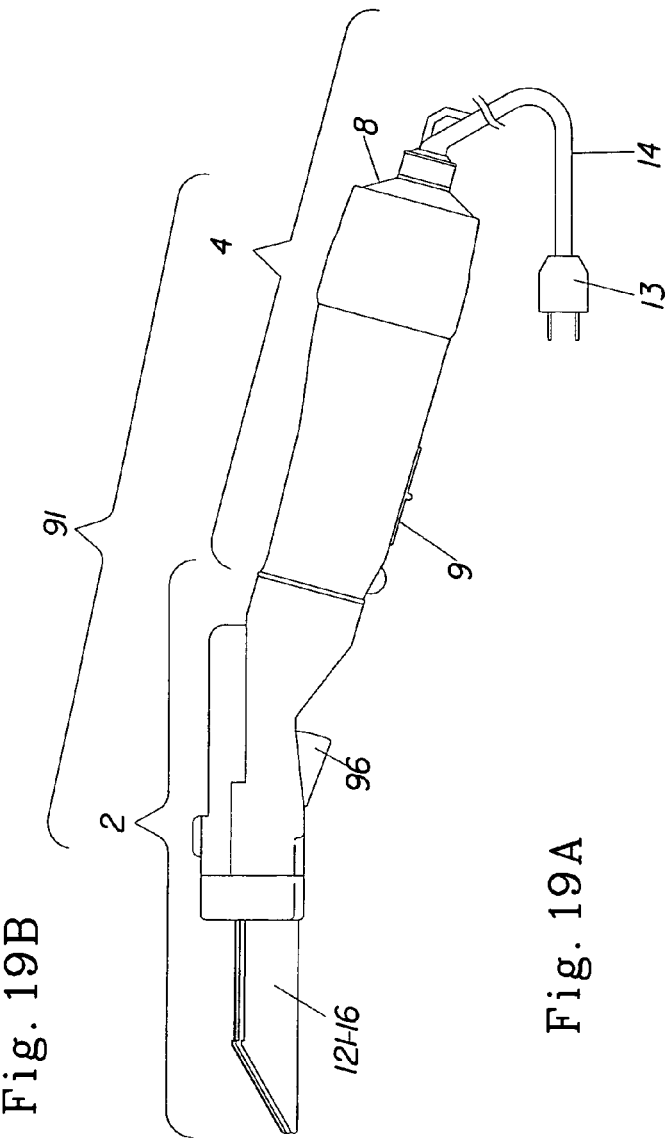
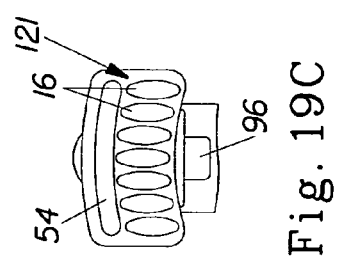
Fig. 19B
Fig. 19A
Fig. 19C

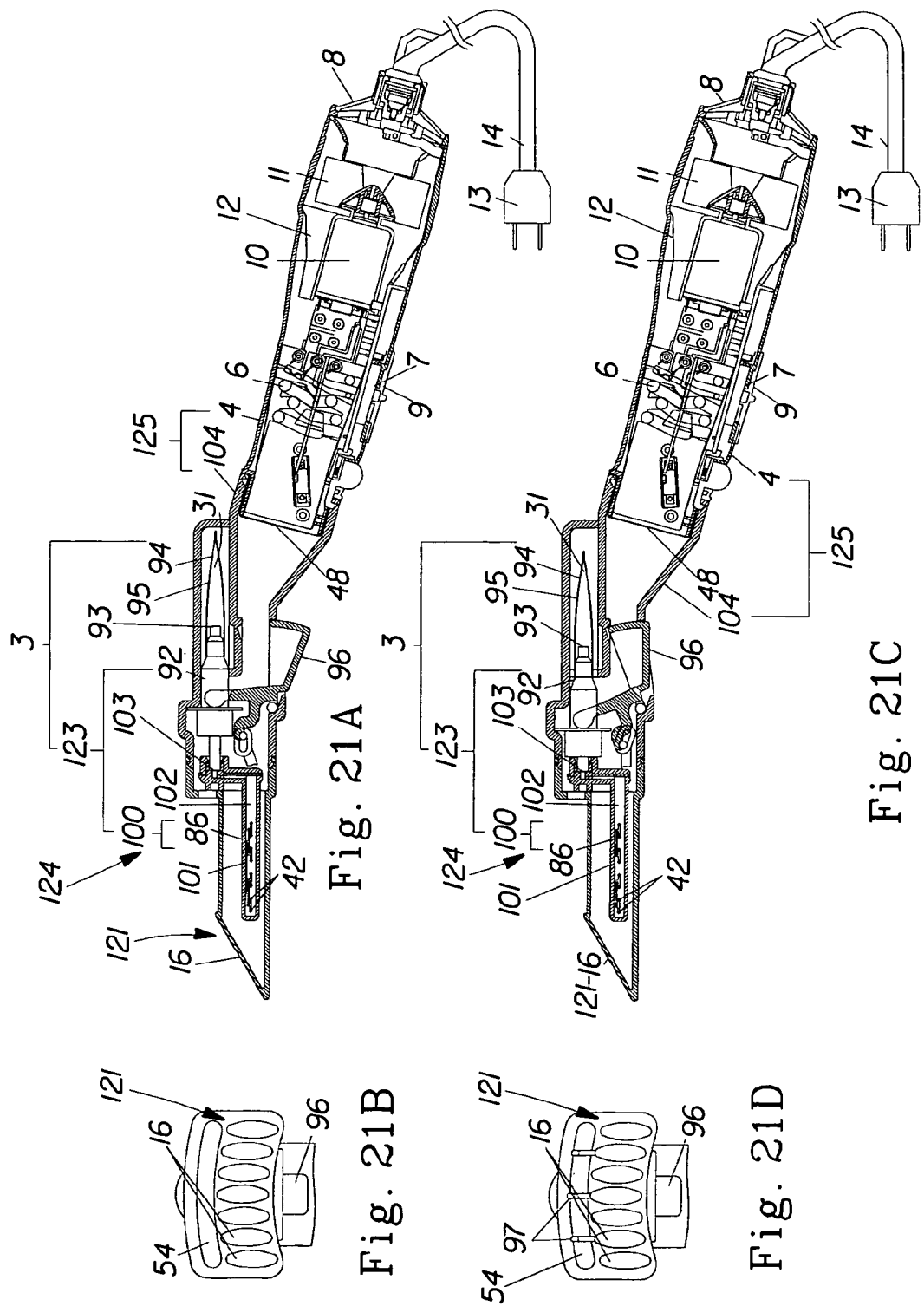

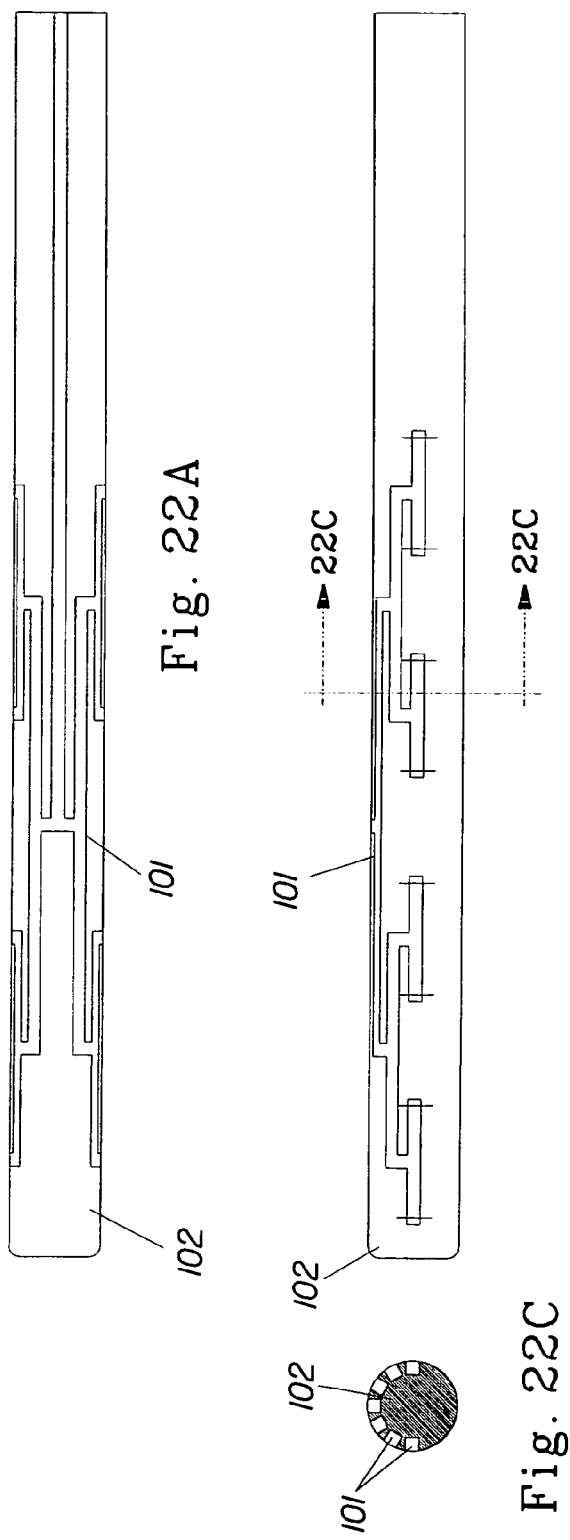

DEVICE FOR ACHIEVING LIFT AND VOLUME TO HAIR

CROSS REFERENCE TO RELATED APPLICATION

The application is a continuation of International application PCT/US03/37759 filed on Nov. 21, 2003.

FIELD OF THE INVENTION

This invention relates to hair styling devices, particularly to a hair styling device capable of using a fixing styling polymer in combination with heat and a hair lifting mechanism to produce volume and lift to the hair.

BACKGROUND OF THE INVENTION

The use of hair styling devices for styling hair is well known and many attempts have been made to provide devices such as hair rollers, curling irons and flat irons with structures to improve the results obtained in curling, straightening, and setting hair with the aid of air or heat.

In order to achieve a desired lift and volume to the hair, attempts in the past have used the combination of hair styling products such as mousses, gels and sprays in combination with a hair styling device such as a dryer, curling iron, or flat iron. However, the result of using this method is cumbersome and results in a very limited and not long-lasting through the day hair style.

It has now surprisingly been found a single hair styling device can achieve this unmet need. The present invention discloses a hair styling device for providing lift to a mass of undifferentiated hair stands on a scalp region comprising: a bundling means for gathering hair strands into hair bundles; a reservoir, in fluid communication with the bundling means, comprising a styling composition; and a means to hold and further align the hair strands along and beyond the bundling means.

This approach allows for the delivery of a thin layer of active on the hair, close to the scalp and results in a long-lasting hair style throughout the day. This approach also eliminates the problems associated with the use of too much styling product all over the hair, which will have a negative impact on the hair feel. The hair styling device of the present invention allows a user to put larger amounts of active (localized deposition) in a specific area to provide lift and volume benefits while minimizing feel tradeoff.

SUMMARY OF THE INVENTION

The present invention is directed to a hair styling device for providing lift to a mass of undifferentiated hair stands on a scalp region comprising: a bundling means for gathering hair strands into hair bundles; a reservoir, in fluid communication with the bundling means, comprising a styling composition; and a means to hold and further align the hair strands along and beyond the bundling means.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify like elements and wherein:

FIG. 2C is an exploded side view of a hair styling device according to the present invention comprising a tine assembly and a delivery system.

FIG. 2D is a further exploded side view of a hair styling device according to the present invention comprised of a tube set, a driving means and reservoir.

FIG. 6A is a side view, with one tine removed, showing the use of a hair styling device according to the present invention, showing the hair styling device inserted in hair, resting on scalp.

FIG. 6B is a front elevational view showing the use of a hair styling device according to the present invention, showing the hair styling device inserted in hair resting on scalp.

FIG. 10A is a longitudinal view of an embodiment of the present invention wherein the bundling means may provide either air or styling composition.

FIG. 10B is a front elevational view an embodiment of the present invention.

FIG. 11A is a longitudinal view of an embodiment of the present invention comprising tines that function as a means to further align and hold.

FIG. 11B is a front elevational view of an embodiment of the present invention comprising tines that function as a means to further align and hold.

FIG. 12A is a top view of an embodiment of the present invention comprising a reservoir with a bundling means.

FIG. 12B is a longitudinal cross-sectional view of an embodiment of the present invention, taken along line G-G of FIG. 12A, comprising a reservoir within the bundling means.

FIG. 12C is a transverse cross-sectional view of an embodiment of the present invention taken along line B-B of FIG. 12B.

FIG. 13A is a view of an embodiment of a hair styling device according to the present invention comprising a reservoir.

FIG. 13B is a longitudinal cross-sectional view of an embodiment of a hair styling device according to the present invention taken along dotted line D-D of FIG. 13A.

FIG. 13C is view of an embodiment of a hair styling device according to the present invention comprising a container for containing styling composition with an outlet and a pipe.

FIG. 13D is a transverse cross-sectional view of an embodiment of a hair styling device according to the present invention taken along dotted line E of FIG. 13C.

FIG. 13E is a top view if an embodiment of the present invention comprising a container.

FIG. 13F is a top view of an embodiment of a hair styling device according to the present invention comprising a reservoir.

FIG. 14A is a longitudinal cross-sectional view of an embodiment of a hair styling device according to the present invention comprising a movable plate beneath tines.

FIG. 14B is a front elevational view of an embodiment of a hair styling device according to the present invention comprising a movable place beneath tines.

FIG. 14C is a longitudinal cross-sectional view of an embodiment of a hair styling device according to the present invention comprising a movable plate below the tines and displaced from tines.

FIG. 14D is a front elevational view of an embodiment of a hair styling device according to the present invention comprising a movable plate below the tines and displaced from tines.

FIG. 17A is a longitudinal cross-sectional view along line F-F of FIG. 17B of tines in an embodiment of a hair styling device according to the present invention comprising a means to further align and hold hair between tines.

FIG. 17B is front elevational view of an embodiment of a hair styling device according to the present invention comprising a means to further align and hold hair set between tines.

FIG. 17C is a longitudinal cross-sectional view of tines in an embodiment of a hair styling device according to the present invention comprising a means to further align and hold hair being raised between tines.

FIG. 17D is a front elevational view of an embodiment of a hair styling device according to the present invention comprising a means to further align and hold being raised between tines.

FIG. 18B is an enlarged view of a longitudinal cross-sectional view of an embodiment of a hair styling device according to the present invention taken along section H of FIG. 18A.

FIG. 18C is a transverse cross-sectional view of a hair styling device according to the present invention taken along dotted line G-G of FIG. 18B.

FIG. 19A is a side view of an embodiment of a hair styling device according to the present invention comprising a bundling means, and means to further align and hold, a button and a reservoir.

FIG. 19B is a top view of an embodiment of a hair styling device of FIG. 19A according to the present invention comprising a bundling means and means to further align and hold.

FIG. 19C is a front elevational view of an embodiment of a hair styling device of FIG. 19A according to the present invention comprising a bundling means, an air outlet, and a button.

FIG. 21A is a longitudinal cross-sectional view of an embodiment of a hair styling device according to the present invention, taken along line K-K of FIG. 19B.

FIG. 21B is a front elevational view of an embodiment of a hair styling device according to present invention comprising a bundling means, an air outlet, and a button.

FIG. 21C a longitudinal cross-sectional view of an embodiment of a hair styling device according to the present invention, taken along line K-K of FIG. 19B, wherein a button has been actuated.

FIG. 21D is a front elevational view of an embodiment of a hair styling device according to the present invention comprising a bundling means, an air outlet, and a button.

FIG. 22A is an exploded longitudinal cross-sectional view of an applicator means according to the present invention comprising a rod and a ditch.

FIG. 22B is an enlarged longitudinal side view of Part M of FIG. 21C.

FIG. 22C is a transverse cross-sectional view of an applicator means according to the present invention taken along dotted line L-L of FIG. 22B.

DETAILED DESCRIPTION OF THE INVENTION

All documents cited are, in relevant part, incorporated herein by reference; the citation of any document is not to be construed as an admission that it is prior art with respect to the present invention.

All ratios are weight ratios unless specifically stated otherwise.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more" The present invention can comprise, consist of, or consist essentially of the essential elements and limitations of the invention described herein, as well any of the additional or optional ingredients, components, or limitations described herein.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials. Herein, "molecular weight" means weight average molecular weight, unless specifically stated otherwise.

The components, including those, which may optionally be added, of the methods of the present invention, as well as methods for preparation, and methods for use, are described in detail below.

Other advantages and novel features of the present invention will become apparent to those skilled in the art from the following detailed description, which simply illustrates various modes contemplated for carrying out the invention. As will be realized, the invention is capable of other different aspects, all without departing from the spirit and scope of the invention. Accordingly, the drawings and descriptions are illustrative in nature and not restrictive.

Reference will now be made in detail to various exemplary embodiments of the invention, several of which are also illustrated in the accompanying drawings, wherein like numerals indicated the same elements throughout the views.

Figure 1A:
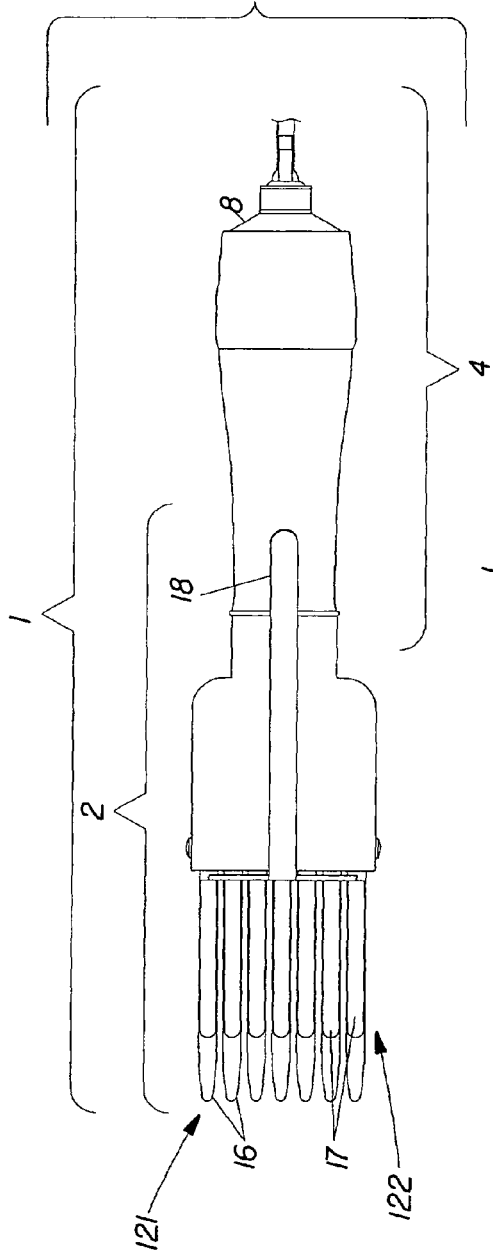
FIG. 1A is a top view of a hair styling device according to the present invention.
Figure 1B:
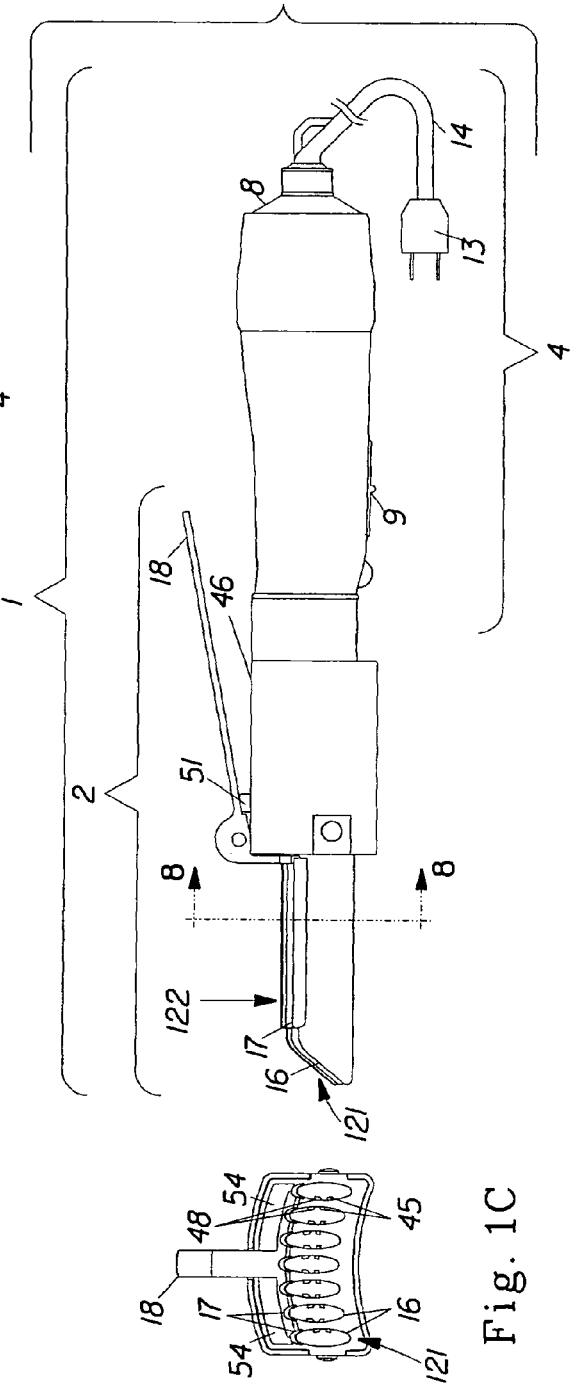
FIG. 1B is a side view of a hair styling device according to the present invention.
Figure 1C:
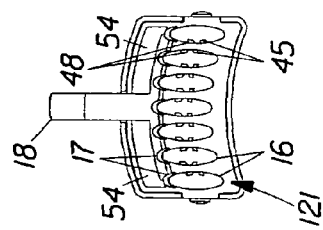
FIG. 1C is a transverse cross-sectional taken along dotted line B of FIG. 1B.

FIGS. 1A, 1B, 1C, 2A, 2B, 2C, 2D, and 3 depicts non-limiting exemplary embodiment of a hair styling device of the present invention, FIGS. 1A, 1B, IC, 2A, 2B, 2C, 2D, and 3 demonstrate an outline of a device (1). A device (1) comprises an attachment (2) connected to a means to set (4). The attachment (2) is comprised of a bundling means (121), a means to further align/hold (122), and a delivery system (3). Delivery system (3) may be set inside of a tine assembly (47). Delivery system (3) may be placed on or taken off tine assembly (47). Likewise, attachment (2) can be placed on and taken off a means to set (4). A means to set (4) may comprise any conventional means to set the styling composition such as a dryer or a heat plate. Wherein the means to set (4) may be a dryer it may comprise an air flow apparatus (5), a heater (6) and a switch (7) inside of a dryer. The means to set (4) may be a dryer which comprises an air inlet (8) at one of end of the dryer. The means to set (4) may be a dryer comprising a first air outlet (49) at the opposite end of the means to set (4) from the air inlet (8). The means to set (4) may comprise a switch (7) connected with a switch plate (9) that is placed on a side of the means to set (4). When the switch plate (9) is moved, switch (7) may be turned to an on position or an off position. Air flow apparatus (5) may comprise a motor (10), a fan (11), and an air flow regulator (12). When the switch (7) is in an on position, the motor (10) and heater (6) may be turned on from an external electrical power source through a plug (13) and a power cord (14). A fan (11) is connected with the motor (10). The motor (10) may turn the fan (11). Air (50) may arise from turning of the fan (11). Air (50) may enter in at the air inlet (8) and go through the fan (11) and air flow regulator (12) and reach the heater (6). Air (50) is rectified by an air flow regulator (12). Air (50) that may reach the heater (6) is heated in temperature by the heater (6). An air source delivers air in a temperature range of about 25° C. to about 140° C. Air (50) that is heated by the heater (6) may reach the first air outlet (49).

Figure 4:
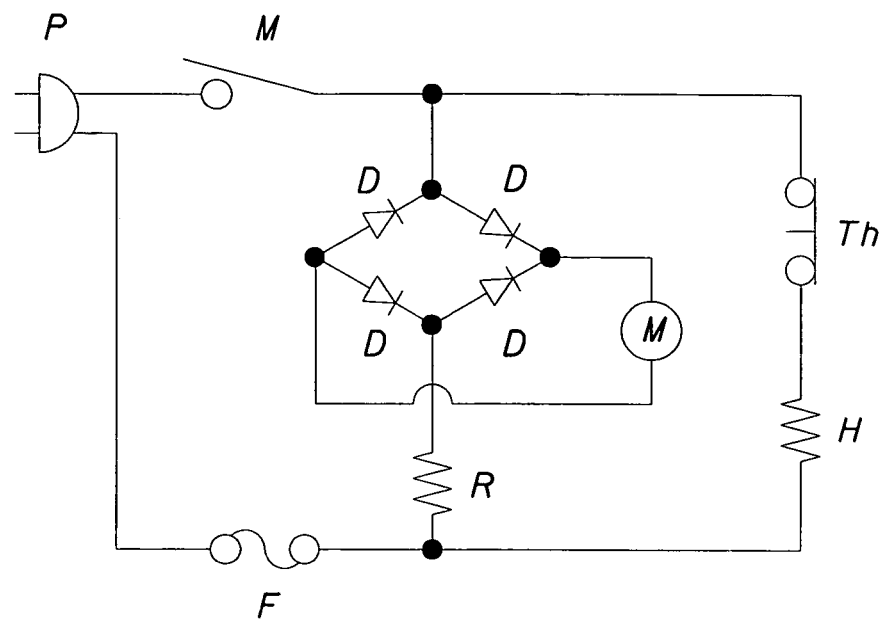
FIG. 4 is a schematic diagram of electrical wiring arranged to conduct current to heat generating resistance wire according to the present invention.

FIG. 4 depicts non-limiting exemplary embodiment of a hair styling device of the present invention. FIG. 4 depicts a schematic circuit drawing arranged to conduct current to the hair styling device of the present invention. The electronics is comprised of a plug (P), (S), (F) and (R), a diode (D), a motor (M), a thermostat (Th) and a heater (H).

Bundling Means

Figure 2A:
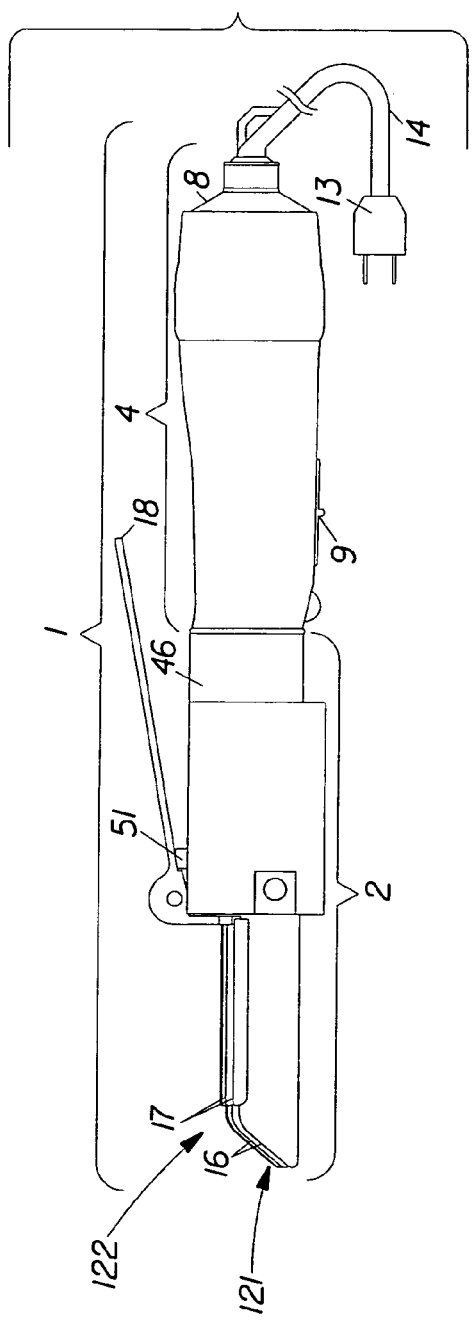
FIG. 2A is a side view of a hair styling device according to the present invention.
Figure 2B:
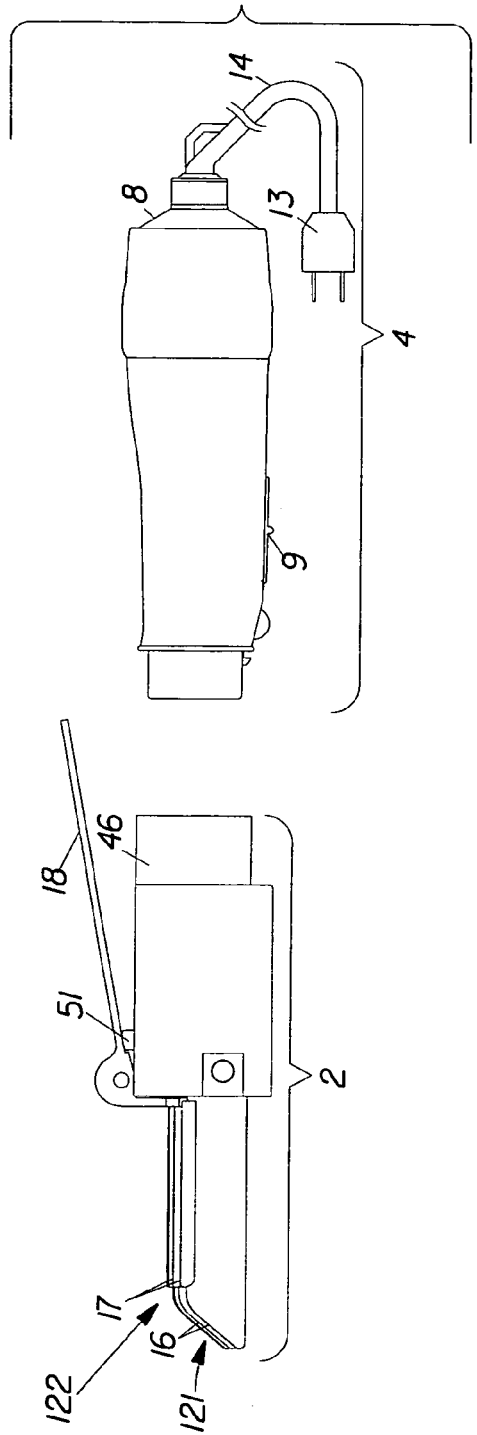
FIG. 2B is an exploded side view of a hair styling device according to the present invention comprising the bundling means and means to dry.
Figure 5C:
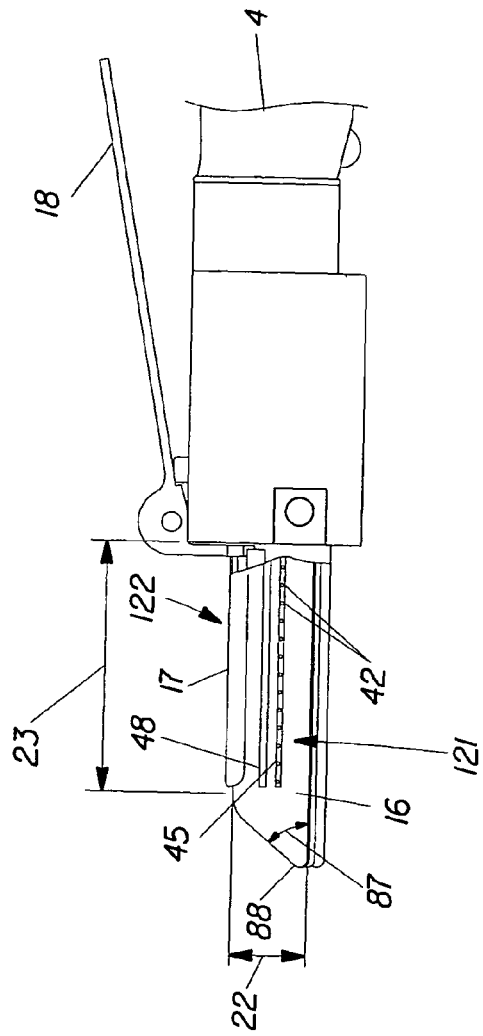
FIG. 5C is a longitudinal view, with one tine removed, of a hair styling device according to the present invention.
Figure 5A:
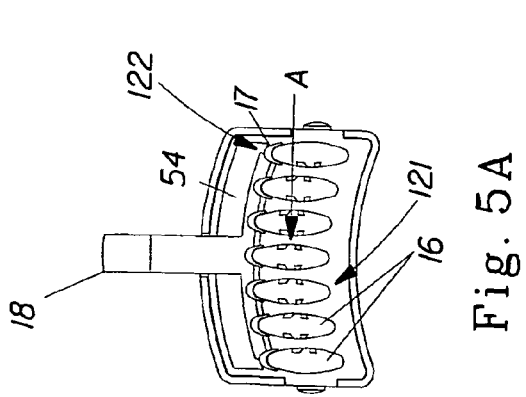
FIG. 5A is a front elevational view of a tines and lift plate according to the present invention
Figure 5B:
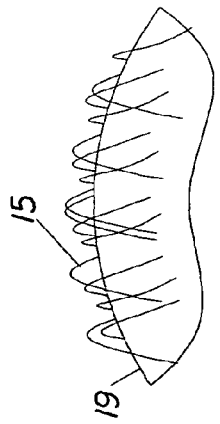
FIG. 5B is a top view of a scalp with untreated hair.

FIGS. 5A, 5B, 5C and FIGS. 6A and 6B depict non-limiting exemplary embodiments of a hair styling device of the present invention. FIGS. 5A, 5B, and 5C depicts a device (1) and hair strands (15) shown before inserting the device (1). FIG. 6 depicts the device (1) inserted into the hair strands (15). In an embodiment of the present invention, a bundling means (121) may be comprised of a tines (16). A tine assembly (47) is comprised of tines (16), a lift plate (17), a lever (18) and a base (46) (as shown in FIG. 2A). The tines (16) are inserted into the hair strands (15). The tines (16) are placed parallel to a scalp (19). The tines (16) may touch the scalp (19). First distance (20) in FIG. 6 determines the scalp (19) field that is between the center of adjacent tines (16). The hair strands (15) at that field determined by the first distance (20) are grouped or bundled together to second distance (21) between the adjacent tines (16). When the tines (16) are placed in the hair strands (15), the hair strands (15) in first distance (20) is bundled up which may result in added lift and added volume to the hair (15).

Tines

A height (22) of the tines (16) may determine the amount of lift and volume applied to the hair strands (15). Therefore the height (22) of tines (16) is determined to provide the lift and volume to the hair strands (15) that a user may desire. The hair strands (15) bundle is made between adjacent tines (16) and at a height (22). The second distance (21) between tines (16) may be set at the appropriate distance so that it will provide adequate hair bundling while allowing adequate ease for inserting the device through the hair strands (15). The second distance (21) may be in range of from about 1.0 mm to about 2.5 mm. In a further embodiment, the second distance (21) may be about 1.5 mm. A length (23) of the flat face on tine (16) and a third distance (24) between the centers of the tines (16) located at both ends of tines (16) may determine effective area at one cycle of use. Radius 25 may be a size fitting curve of a scalp (19). An acute angle tip (88) of tines (16) may assist in achieving easy insertion of tines (16) into hair strands (15). A smaller angle (87) of a tines tip (88) may also assist in achieving easy insertion of tines (16) into hair strands (15). The smaller angle (87) of a tines tip (88) may be in a range from about 20 degrees to about 90 degrees. In a further embodiment, the smaller angle (87) of a tines tip (88) may be in a range from about 25 degrees to about 45 degrees. The tines are about 20 mm in height. The tines are from about 85 mm to about 90 mm in length. The tines are from about 5 mm to about 10 mm in width.

Means to Hold and Further Align

Figures 7A, 7B:
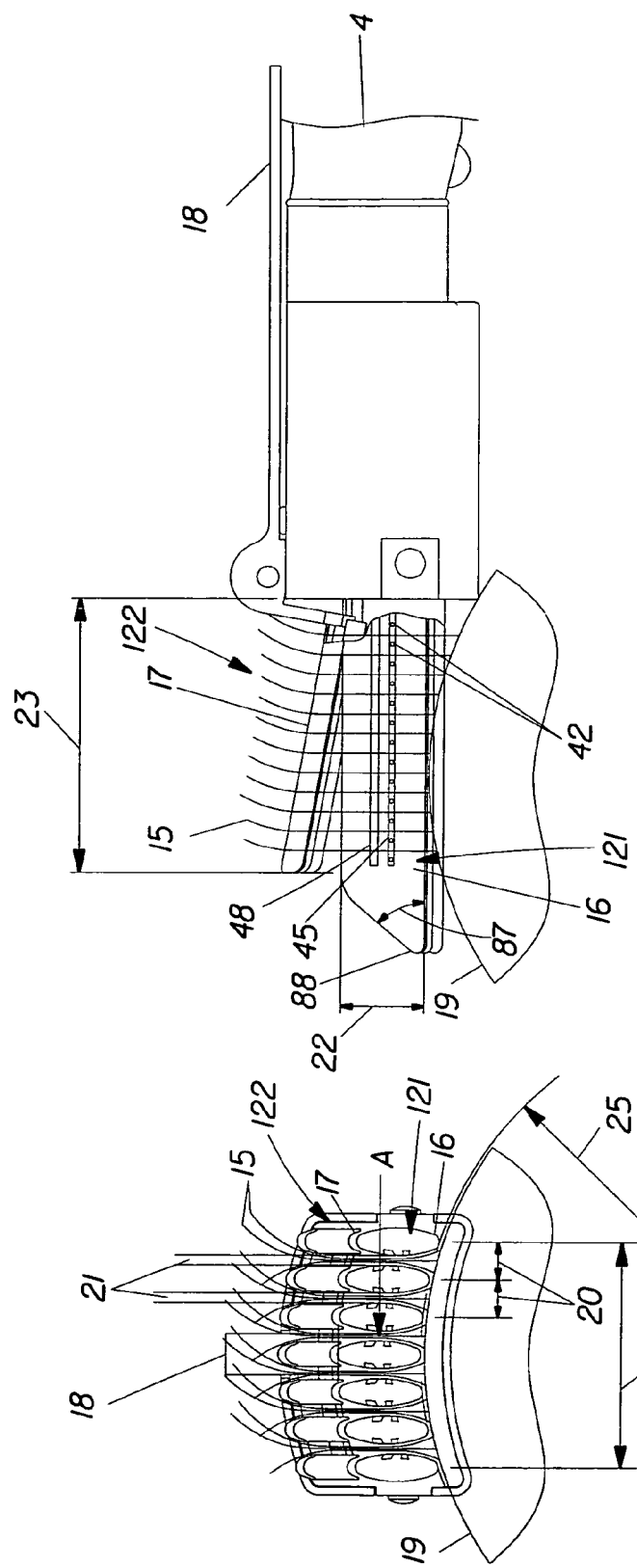
FIG. 7A is a longitudinal view, with one tine removed, showing the use of a hair styling device according to the present invention, showing the hair styling device inserted in hair with a means to further align and hold the hair.
FIG. 7B is a is a front elevational view showing the use of a hair styling device according to the present invention, showing the hair styling device inserted in hair at the scalp region with a means to further align and hold the hair.
Figure 23A:
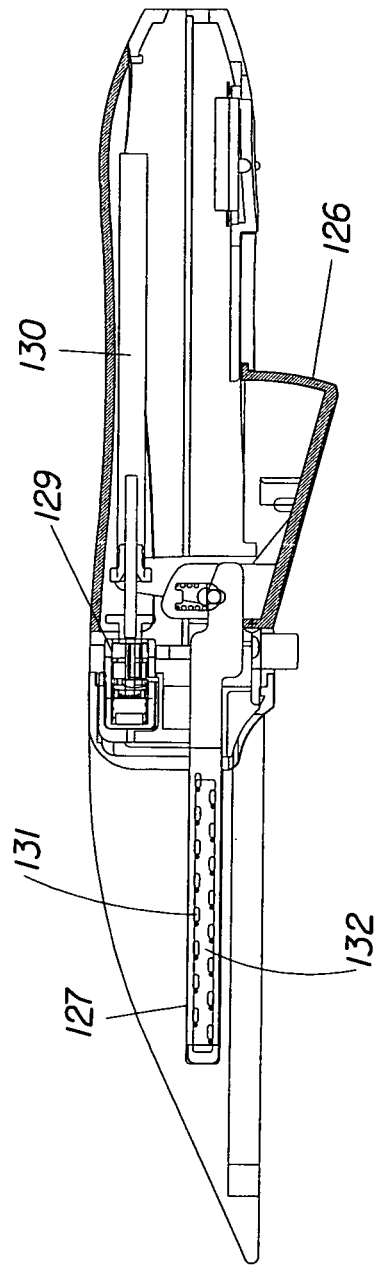
FIG. 23A is a longitudinal cross-sectional view of an embodiment of a hair styling device according to the present invention comprising a lever, a heat plate, a pump and a reservoir.
Figure 23B:
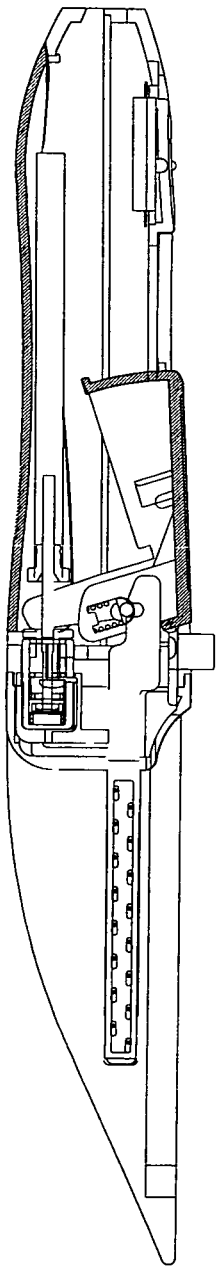
FIG. 23B is a longitudinal cross-sectional view of an embodiment of a hair styling device according to the present invention wherein a lever has been actuated.
Figure 23C:
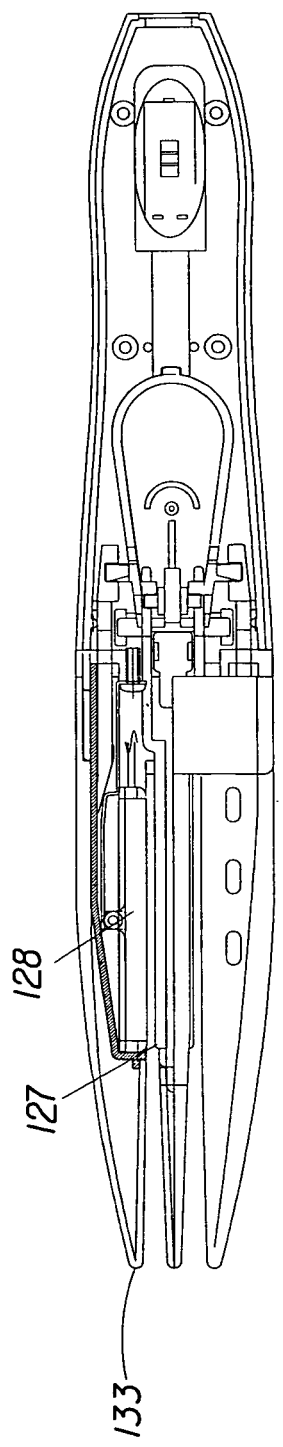
FIG. 23C is a top longitudinal cross-sectional view of an embodiment of a hair styling device according to the present invention comprising a shutter and a heat plate.
Figure 23D:
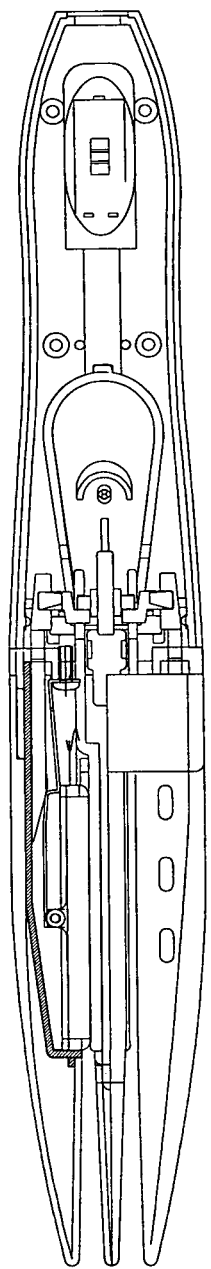
FIG. 23D is a top longitudinal cross-sectional view of an embodiment of a hair styling device according to the present invention wherein a lever has been actuated.

FIGS. 7A and 7B depicts a non-limiting exemplary embodiment of a hair styling device of the present invention. In an embodiment of the present invention, the means to hold and further align (122) the hair strands may be hingedly connected to the bundling means (121). The means to hold the hair strands is displaced from about 0 to about 10 mm from the bundling means. In an embodiment of the present invention, a means to hold and further align (122) may be comprised of a lift plate (17). In an embodiment of the present invention, the action of holding and further aligning the hair may be achieved by a lift plate (17) which may be displaced from the hair styling device in a vertical manner or achieved by a heat plate (128) (FIG. 23C) which may be displaced horizontally or in parallel displacement with the scalp. In a further embodiment, the means to hold and further align (122) the hair strands provides alignment of the hair bundles substantially orthogonal to a scalp. FIGS. 7A and 7B depicts an embodiment wherein a lift plate 17 is raised or elevated. Lift plate (17) may be placed on tines (16) and is parallel with tines (16) as shown in FIGS. 1A, 1B, 1C and FIG. 3. The lift plate (17) is connected with lever (18) to the device. In a further embodiment of the present invention, the means to hold and further align may be hingedly connected to a bundling means (121). The lift plate (17) is in contact with tines (16) when the lever (18) is not pressed down. The lift plate (17) is moved above the tines (16) and pulls the hair strands (15) when the lever (18) is pressed down. The hair strands (15) bends when the lift plate (17) is not moved about the tines (16), as shown in FIGS. 6A and 6B The hair strands (15) is pulled and is made straight by the lift plate (17) when the lift plate (17) is moved above tines 16.

Delivery System

Figure 3:
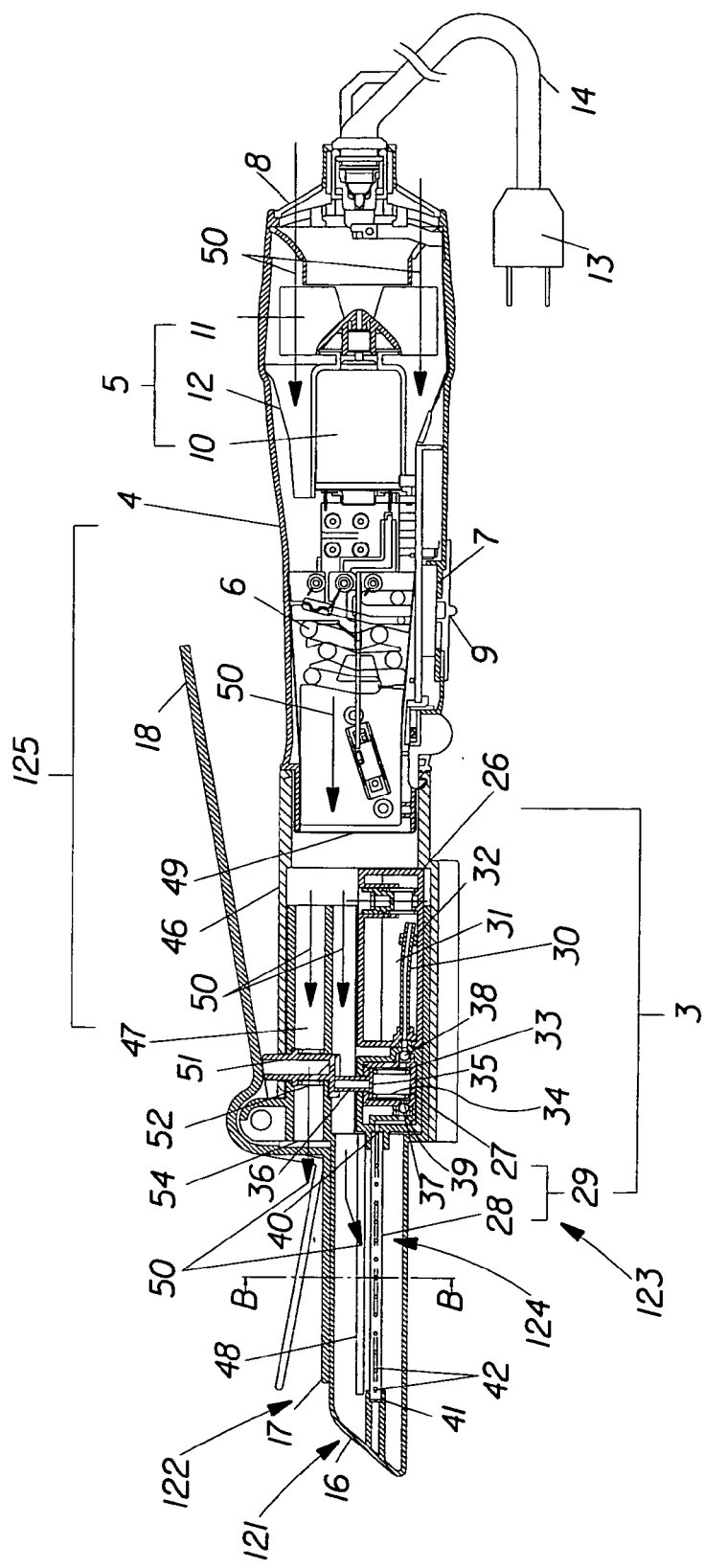
FIG. 3 is a longitudinal cross-sectional view of a hair styling device according to the present invention.

A delivery system (3) may be comprised of a reservoir (26), a pump (27) and capillary tubes (28), as depicted in FIG. 3. A pump (27) and capillary tubes (28) may make a set, namely a tube set (29). The tube set (29) may be placed on and taken off a reservoir (26). The pump (27) is connected with the reservoir (26). A hose (30) may be placed in the reservoir (26). A styling composition (31) may be placed in the reservoir (26). The reservoir (26) may be in fluid communication with the bundling means. One of the ends of a hose (30) may be connected with the pump (27). The pump (27) may be connected with the capillary tube (28) at another side. One end of the hose (30) may be soaked in styling actor 30. The hose (30) may have a weight (32) at a side of the styling composition (31). The pump (27) may comprise a case (33), a piston (34), a first spring (35), a shaft (36), and a first ball (37) and second ball (38). The shaft (36) may be connected with the piston. When the shaft (36) is pushed, piston (34) may push the first spring (35) and the piston (34) will be down inside of the case (33). When the shaft (36) is released, the piston (34) may be pushed up by a first spring (35). When the piston (34) is pushed up, the first ball (37) at the side of the capillary tube (28) closes a ball (39) of case (33). Second ball (38) at the side of the reservoir (26) is sucked up. The styling composition (31) comes into case (33) from the reservoir (26) through the hose (30). When the piston (34) is raised up again, the styling composition (31) in case 33 may be pushed out to the capillary tube (28).

Capillary Tube Description

Figure 8:
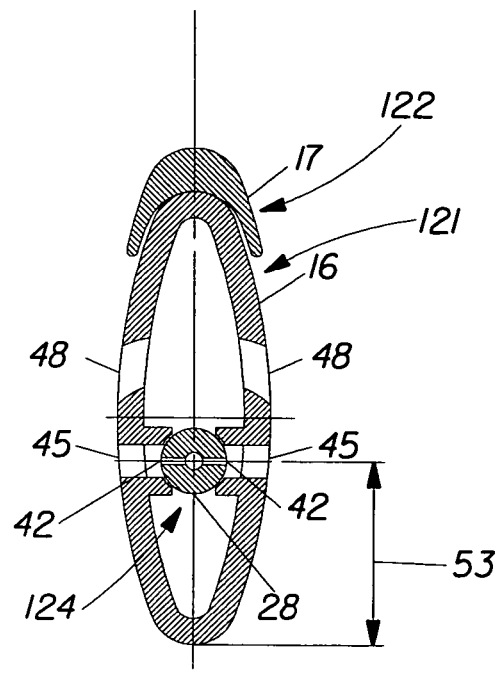
FIG. 8 is a transverse cross-sectional taken along dotted line B of FIG. 1B.
Figure 9:
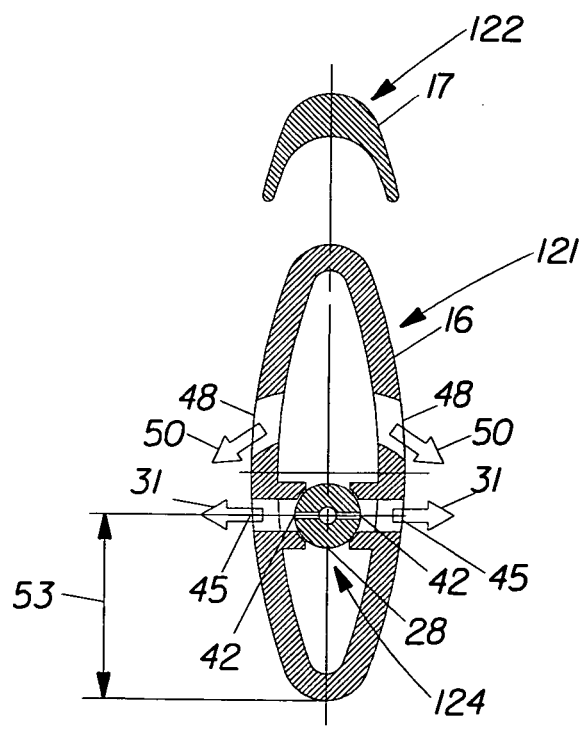
FIG. 9 transverse cross-sectional taken along dotted line 9A-9A of FIG. 7A.

FIG. 3 depicts a non-limiting exemplary embodiment of a hair styling device of the present invention. In an embodiment, the applicator means (124), is in fluid communication with a reservoir (26), for applying the styling composition (31) to the hair strands (15). In an embodiment of the present invention, an applicator means (124) may be comprised of a capillary tube (28), which supplies the styling composition (31) to the hair strands (15). A driving means (123) may transport the styling composition through the applicator means from the reservoir (26). In a further embodiment of the present invention, a driving means (123) may be comprised of a pump (27) that transports the styling composition (31) to an application means (124). FIG. 8 and FIG. 9 depict cross-section drawings depicting this embodiment. The capillary tube (28) is hollow. A first end (40) of capillary tube (28) may be open and a second end (41) may be closed. The capillary tube (28) may be set inside of tines (16). The capillary tube (28) may be set parallel to tines (16). The first end (40) of the capillary tube (28) is connected with a driving means (123) which may be a pump (27). The capillary tube 28 has plural outlet (42) of the styling composition (31) on a side of the capillary tube (28). The plural outlet (42) is a hole that goes through a wall of capillary tube (28). Diameter (43) of plural outlet (42) may be about 0.3 mm. Internal diameter (44) of capillary tube (28) may be about 0.8 mm. Plural outlet (42) may be set up in line one side of the capillary tube (28) or in another embodiment, plural outlet (42) may be set up in line on both sides of the capillary tubes (28). Tines (16) may comprise an outlet (45)

comprising styling composition (31) at the sane position as plural outlet (42) on capillary tube (28). The styling composition (31) is sent into the capillary tube (28) from the reservoir (26) by the pump (27). The styling composition (31) goes out from each plural outlet (42) and pump (27) applies pressure to the styling composition (31) at each plural outlet (42) to force out the styling composition (31). As lever (18) is pressed downward, lever (18) pushes stick (51). As lever (18) is released from pressure, stick (51) is raised up by a second spring (52). The stick (51) is connected with a shaft (36) of pump (27). The shaft (36) has the same movement as the stick (51). As a result, pump (27) may be operated by lever (18). In a further embodiment of the present invention, the styling composition (31) may be releasably held within a reservoir (26), the reservoir (26) comprising fluid-impermeable walls.

The styling composition (31) that the pump (27) carried into the capillary tube (28) goes from plural outlet (42) of capillary tube (28) and is applied to the hair strands (15). In the instance where the lever (18) is pressed downward, the lift plate (17) pulls and makes hair strands (15) straight, and the styling composition (31) is supplied to the root of the hair strands (15). The height (53) is the distance that the hair strands (15) has the effect of the styling composition (31) and wherein the styling composition (31) does not reach the scalp (19). The height (53) may be in the range of from about 5 mm to about 20 mm. In a further embodiment of the present invention, the height (53) may be about 10 mm.

Means to Set

The air (50) which has been generated by the means to set (4) reaches the tines (16). In an embodiment of the present invention, a means to set (125) that may dry the styling composition (31) and set the hair strands (15) may be comprised of a dryer (4) and a tine assembly (47). The air (50) moves out from a second air outlet (48) at the side of tine (16) and the air (50) reaches the hair strands (15). The third air outlet (54) may be made from the tines (16) root to the tines (16) end. The second air outlet (48) is close in proximity to the plural outlet (42) for the styling composition (31). In this manner the air (50) may reach the styling composition (31) on the hair strands (15). The air (50) from the second air outlet (48) may dry the styling composition (31) on the hair strands (15). The styling composition will set in a range of about 1 seconds to about 20 seconds.

FIG. 3 depicts a non-limiting exemplary embodiment of a hair styling device of the present invention. Device (1) may comprise a third air outlet (54) at the base of the tines (16). Air (50) from the third air outlet (54) dries the styling composition (31) on the hair strands (15). The second air outlets (48) of the side of the tines (16) may be almost covered by the hair strands (15), and the temperature of the device (1) does not rise abnormally, because the air (50) goes out from the third air outlet (54) at the base of the tines (16) and therefore the interior of device (1) may not be comprised of heated air (50).

Additional Tines for Air

Figure 10C:
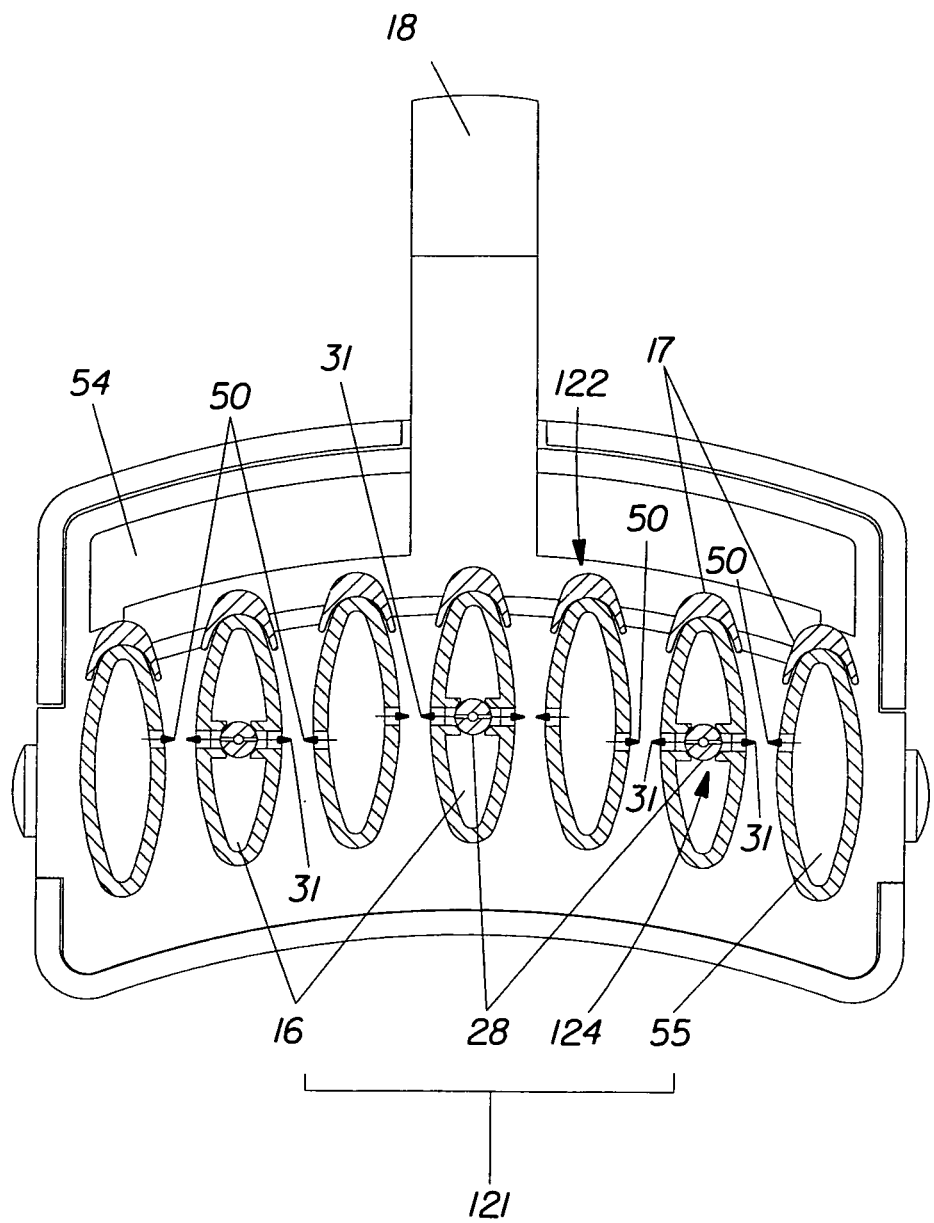
FIG. 10C is a transverse cross-sectional view, on an enlarged scale, taken along dotted line C in FIG. 10A, of an embodiment of the present invention, wherein alternating tines may provide a means to set or a means to bundle.
Figure 11C:
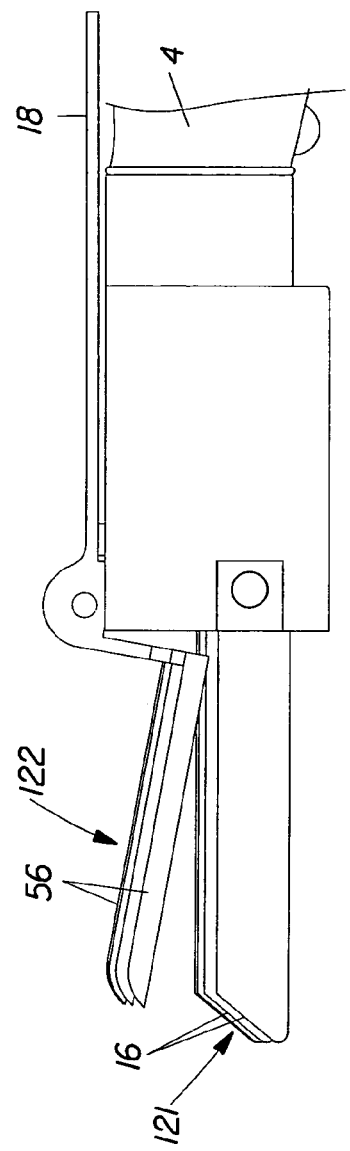
FIG. 11C is a longitudinal view of an embodiment of the present invention comprising tines that function as a means to further align and hold in a raised position.
Figure 11D:
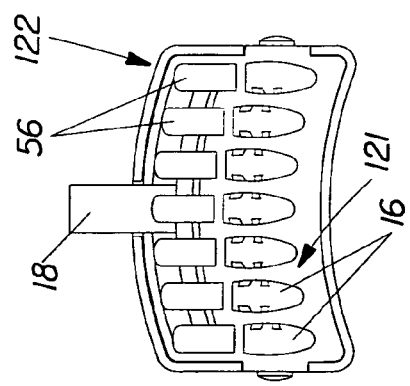
FIG. 11D is a front elevational view of an embodiment of the present invention comprising tines that function as a means to further align and hold in a raised position.
Figure 13G:
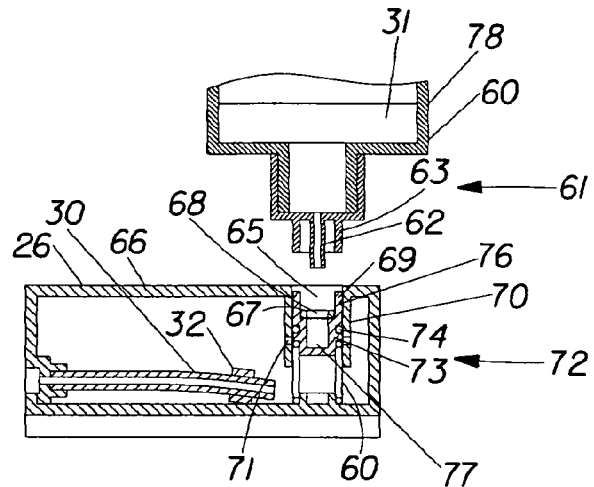
FIG. 13G is a longitudinal cross-sectional view of an embodiment of a hair styling device according to the present invention comprising a refillable reservoir when not linked to a container.
Figure 13H:
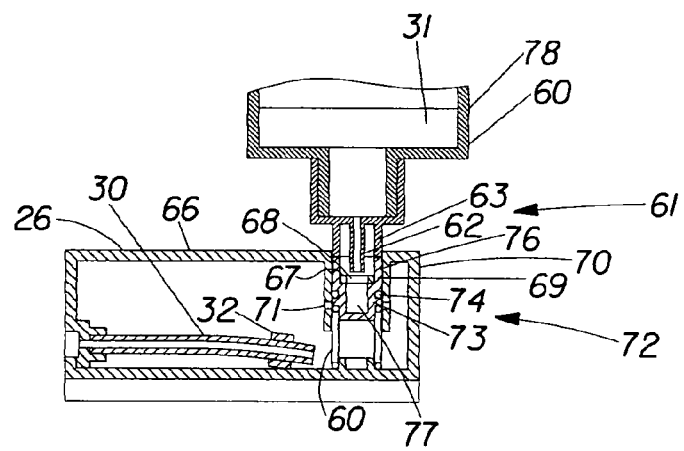
FIG. 13H is a longitudinal cross-sectional view of an embodiment of a hair styling device according to the present invention comprising a re-fillable reservoir when in contact with a container, but no fluid being dispensed from container.
Figure 13J:
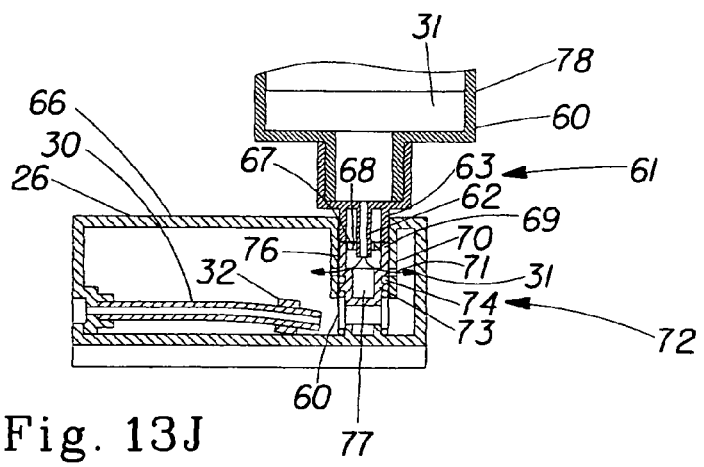
FIG. 13J is a longitudinal cross-sectional view of an embodiment of a hair styling device according to the present invention comprising a re-fillable reservoir when in contact with container and with fluid dispersion from the container.
Figure 15A:
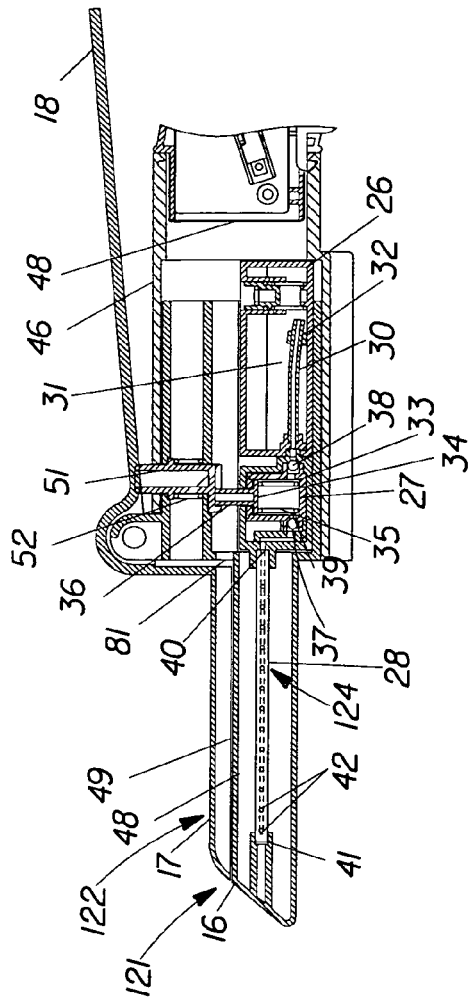
FIG. 15A is a longitudinal cross-sectional view of an embodiment of a hair styling device according to the present invention comprising air outlets located between a bundling means and a means to further align and hold hair and wherein air flows from top of the bundling means.
Figure 15C:
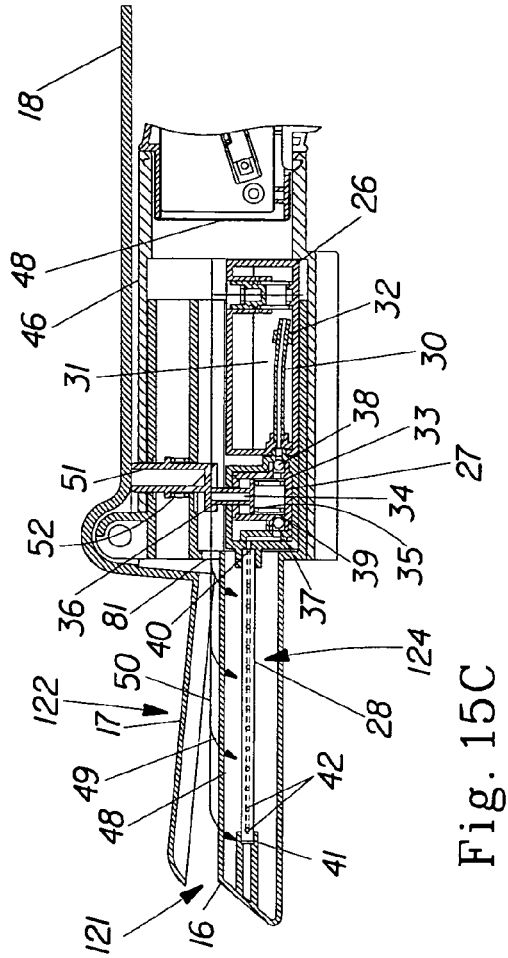
FIG. 15C is a longitudinal cross-sectional view of an embodiment of a hair styling device according to the present invention comprising air outlets which are open to provide air between a bundling means and a means to further align and hold hair.
Figure 15B:
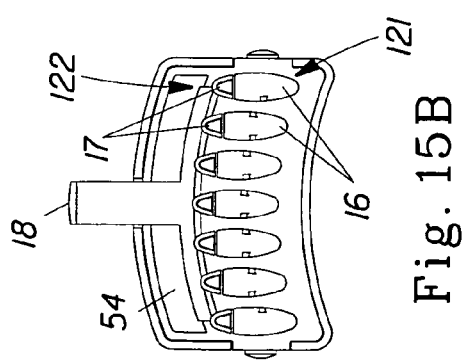
FIG. 15B is a front elevatioanl view of an embodiment of a hair styling device according to the present invention comprising a bundling means and a means to further align and hold hair.
Figure 15D:
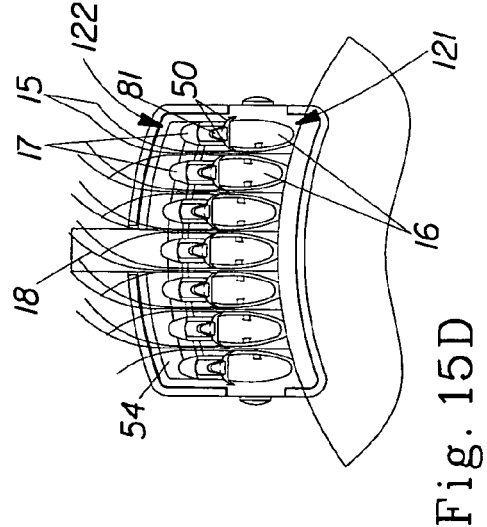
FIG. 15D is a front elevational view of an embodiment of a hair styling device according to the present invention comprising air outlets which are open to provide air between a bundling means and a means to further align and hold hair.

FIGS. 10A, 10B and 10C depicts a non-limiting exemplary embodiment of a hair styling device of the present invention. FIGS. 10A, 10B and 10C depicts an air tines (55) comprising only air (50). An air tines (55) may comprise a second air outlet (48) at both sides of the air tines (55). In the embodiment herein the second air outlet (48) is directed toward the hair strands (15) position that styling composition (31) is delivered wherein the styling composition (31) is readily dried by air (50). In this embodiment of the present invention, a bundling means (121) may be comprised of a tines (16) and an air tines (55).

Second Row of Tines—Means to Hold and Further Align

FIGS. 11A, 11B, 11C and 11D depicts a non-limiting exemplary embodiment of a hair styling device of the present invention. FIGS. 11A, 11B, 11C and 11D depicts a second tines (56) above the tines (16). A second tines (56) may be parallel to the tines (16). The second tines (56) may be horizontally adjacent to the tines (16). The second tines (56) may be connected to the device (1) with a lever (18). The second tines (56) may be moved above the tines (16) and pulls the hair strands (15) when the lever (18) is pressed downward. The hair strands (15) may bend when the second tines (56) is not moved above the tines (16), as depicted in FIG. 6. The hair strands (15) may be pulled and may be made straight by the second tines (56) when the second tines (56) are moved above tines (16). In this embodiment, the means to hold and further align (122) may comprise a second tines (56).

Reservoir is Contained in a Bundling Means

FIGS. 12A, 12B and 12C depicts a non-limiting exemplary embodiment of a hair styling device of the present invention. FIGS. 12A, 12B and 12C depicts a reservoir (26) is comprised in a tines (16). As the reservoir (26) is set inside of the tines (16), hair styling device is reduced in size.

Disposable Reservoir and Refillable Reservoir

FIG. 3 and FIGS. 13A, 13B, 13C, 13D, 13E, 13F, 13G, 13H and 13J depict non-limiting exemplary embodiments of a hair styling device of the present invention. In this embodiment, a delivery system (3) may comprise a reservoir (26). As depicted in FIG. 3, a reservoir (26) can be placed on and removed from a hair styling device of the present invention. In this embodiment, the reservoir (26) is pre-filled with a styling composition (31) and inserted into the hair styling device. When the reservoir (26) is empty, the reservoir (26) can be removed and replaced with another pre-filled reservoir (26), or as termed, a disposable delivery system or non-refillable delivery system.

As depicted in FIGS. 13A, 13B, 13C, 13D, 13E, 13F, 13G, 13H and 13J, a reservoir (26) may comprise a first inlet (58) for injecting a styling composition (31), wherein the user of the hair styling device may refill the reservoir (26) with a styling composition (31). The styling composition (31) may be placed into the reservoir (26) from a bottle (60). A bottle outlet (61) of the bottle (60) may comprise a first pipe (62) and a cylindrical wall (63). A second inlet (64) of the reservoir (26) is dent (65) of reservoir (26) of surface (66). A bottom (67) of the dent (65) comprises openings: one is circular hole (68) at center of bottom (67); other is holes (69) along perimeter of bottom (67). A reservoir (26) may comprise a cylinder (70) that is connected with the dent (65) inside of the reservoir (26). The cylinder (70) may comprise square holes (71) at a side of the cylinder (70). A stopper (72) may be inside of cylinder (70). The stopper (72) comprises a second piston (73) and a rubber ring (74). The stopper (72) may be moved at the inside of cylinder (70). The stopper (72) may be pressed against the bottom (67) by a third spring (75). The second piston (73) may comprise ribs (76) projected from holes (69). A rubber ring (74) may create insulation between the cylinder (70) and the second piston (73). The second piston (73) may comprise a second dent (77) at center of the second piston (73). A wall (63) may be placed into the dent (65), wherein the wall (63) pushes the ribs (76) and the stopper (72) goes down. When the wall (63) reaches the bottom (67), the rubber ring (74) is lower than the holes (71) and the holes (71) are opened. When the wall (63) is placed into the dent (65), a first pipe (62) is placed into holes (68). When a side (78) of bottle (60) is pushed, a styling composition (31) is placed into reservoir (26)

through the first pipe (62) and the holes (71). The typical outlet of another conventional styling composition bottles may be one pipe. However, if the outlet of another conventional styling composition bottle is placed into dent (65), holes (71) are not opened, as stopper (72) cannot be pushed down. Further, a pipe of another conventional styling composition bottle is put into hole (68), stopper (72) cannot be pushed down, as a second dent (77) is deep and a second pipe (72) cannot come in contact with the second piston (73). In the event that reservoir (26) does not have first inlets (58) and reservoir (26) is disposable, this may prevent the use of styling compositions other than styling composition (31). In this embodiment, the above described mechanism prevents the use styling compositions other than styling composition (31).

Means to Hold and Further Align Below Tines

FIGS. 14A, 14B, 14C and 14D depicts a non-limiting exemplary embodiment of a hair styling device of the present invention. FIGS. 14A, 14B, 14C and 14D depicts an embodiment wherein a movable plate (80) is below a tines (16). A movable plate (80) may be connected with a stick (51). When a lever (18) is pressed down, a stick (51) is pressed and the movable plate (80) is displaced from the tines (16). As the movable plate (80) is displaced, movable plate (80) reaches a scalp (19) and tines (16) go up. Tines (16) pull the hair strands (15) when the lever (18) is pushed down. The hair strands (15) is pulled and is made straight by tines (16) when the movable plate (80) is displaced from the tines (16). In this embodiment, a bundling means (121) may comprise a tines (16) and a means to hold and further align (122) may comprise the tines (16) as well.

Air from Top of Bundling Means

FIGS. 15A, 15B, 15C and 15D depicts a non-limiting exemplary embodiment of a hair styling device of the present invention. FIGS. 15A, 15B, 15C and 15D depicts an embodiment wherein the air (50) is dispensed out from a top of the tines (16). A lift plate (17) may be place above a tines (16). A fourth air outlet (81) is set at the base of tines (16). In an embodiment, the fourth air outlet (81) is between the tines (16) and the lift plat (17). Air (50) travels between the space created between the tines (16) and the lift plate (17). Air (50) dries a styling composition (31) on hair strands (15). A volume of air (50) can be increased, because the area of the fourth air outlet (81) can be enlarged.

Air from Bottom of Bundling Means

Figures 16A, 16B:
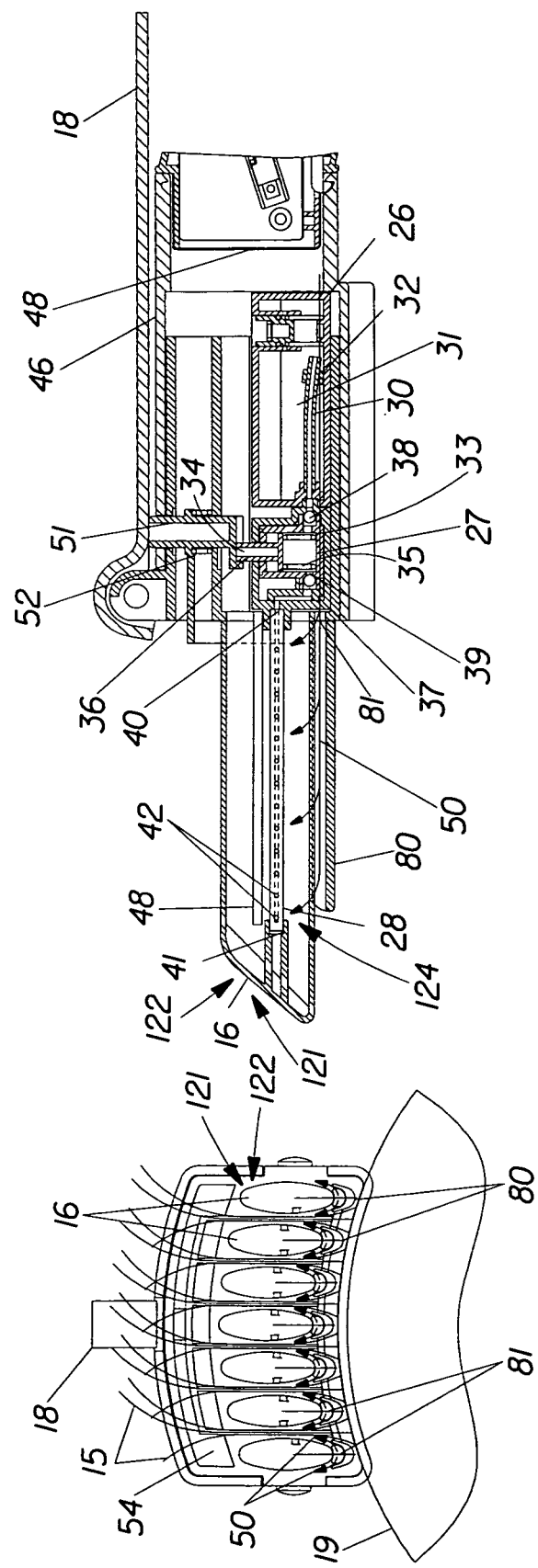
FIG. 16A is a longitudinal cross-sectional view of an embodiment of a hair styling device according to the present invention comprising air outlets located between a bundling means and movable plates located below the bundling means wherein air flows from the bottom of the bundling means.
FIG. 16B is a front elevational view of an embodiment of a hair styling device according to the present invention comprising air outlets providing air between a bundling means and movable plates located below the bundling means.

FIGS. 16A and 16B depicts a non-limiting exemplary embodiment of a hair styling device of the present invention. FIGS. 16A and 16B depicts an embodiment wherein the air (50) is dispensed out from a bottom of the tines (16). A movable plate (80) may be place below tines (16). A fourth air outlet (81) is set at the base of tines (16). In an embodiment, the fourth air outlet (81) is between the tines (16) and the movable plate (80). travels between the space created between the tines (16) and the movable plate (80). Air (50) dries a styling composition (31) on hair strands (15). A volume of air (50) can be increased, because the area of the fourth air outlet (81) can be enlarged. In this embodiment, a bundling means (121) may comprise a tines (16) and a means to hold and further align (122) may comprise the tines (16) as well.

Lift Plate Between Tines

FIGS. 17A, 17B, 17C, and 17D depicts a non-limiting exemplary embodiment of a hair styling device of the present invention. FIGS. 17A, 17B, 17C, and 17D depicts an embodiment wherein a lift plate (17) is set between tines (16). A distance between a scalp (19) and lift plate (17) may be decreased as compared to an embodiment wherein the lift plate (17) is set above the tines (16). Hair strands (15) is pulled and is straightened by lift plate (17). As the distance between the scalp (19) and lift plate is decreased, the embodiment may be effective for achieving volume lift to hair which is short.

Double Structure of Applicator Means

Figure 18A:
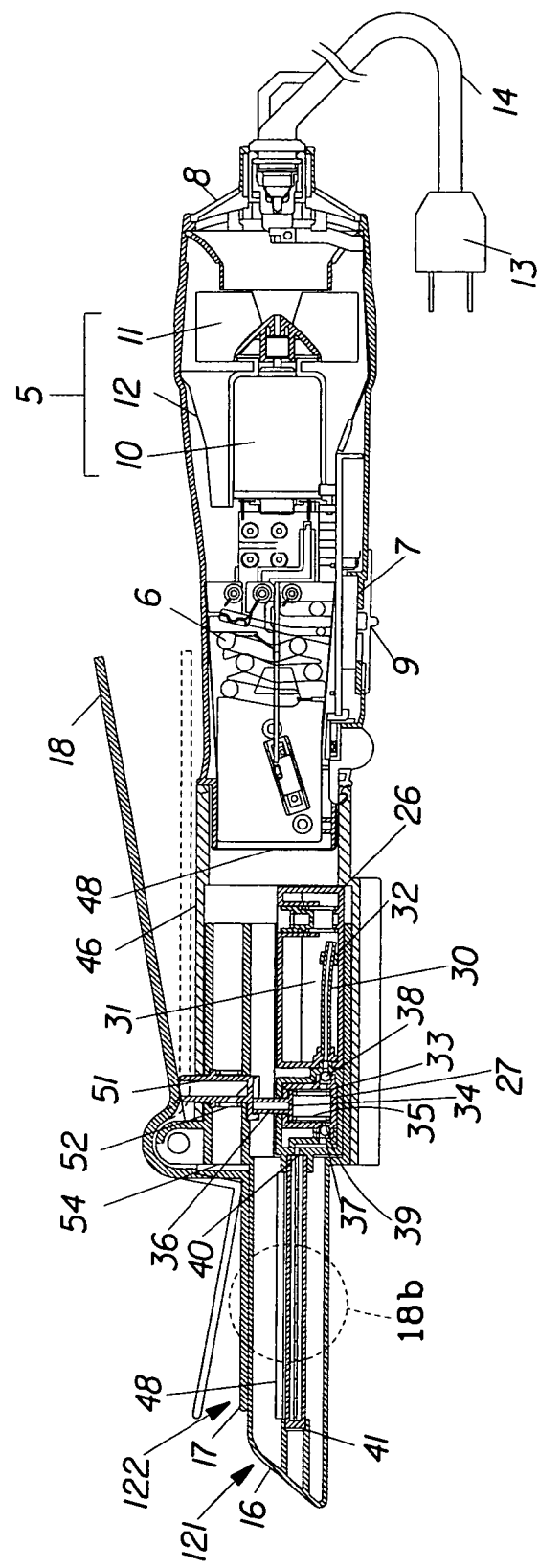
FIG. 18A is a longitudinal cross-sectional view of an embodiment of a hair styling device according to the present invention comprising an applicator means comprising a rod inside of a tube for delivery of a styling composition.
Figure 20A:
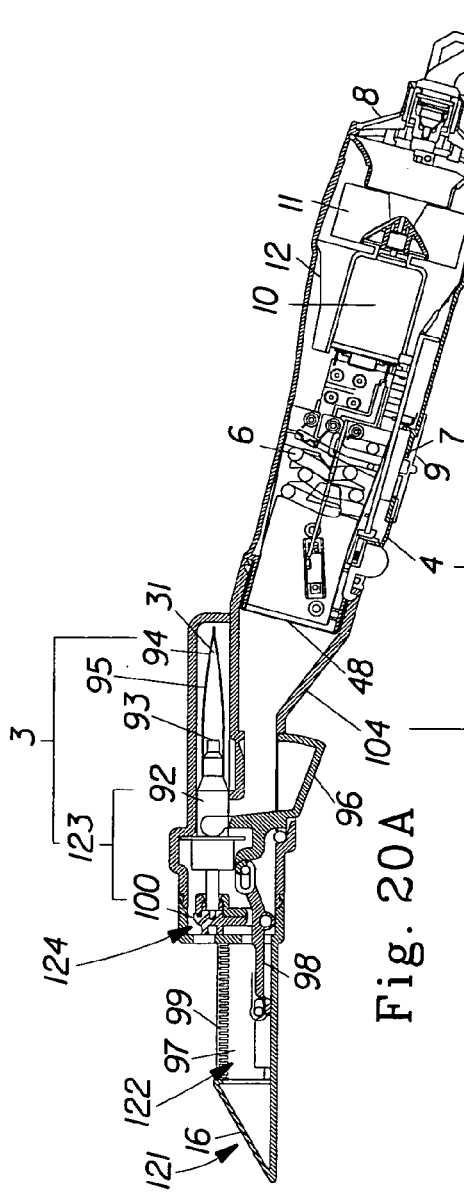
FIG. 20A is a longitudinal cross-sectional view of an embodiment of a hair styling device according to the present invention, taken along line J-J of FIG. 19B.
Figure 20B:
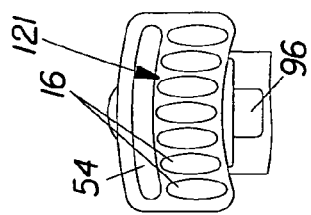
FIG. 20B is a front elevational view of an embodiment of a hair styling device according to present invention comprising a bundling means, an air outlet, and a button.
Figure 20C:
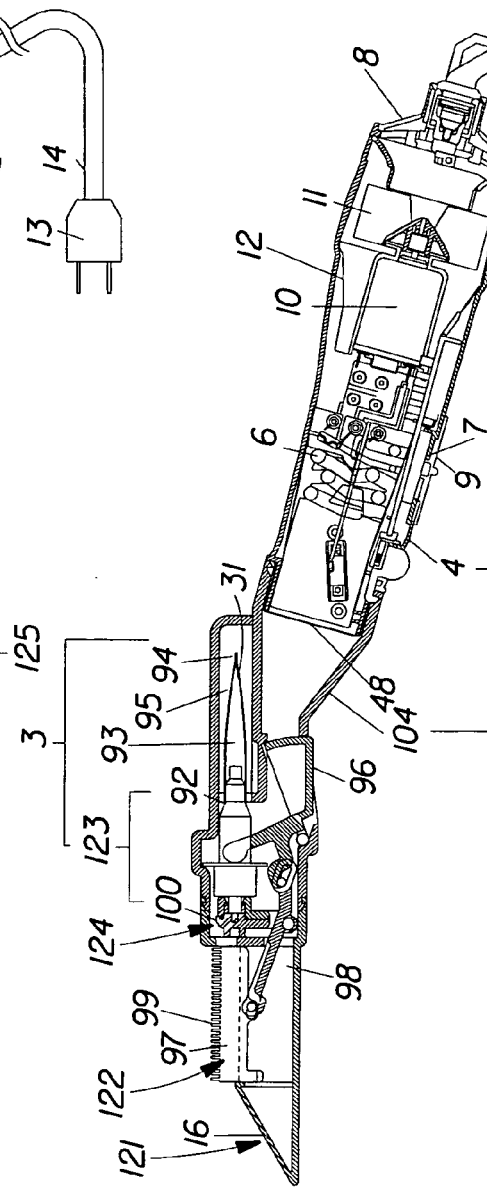
FIG. 20C is a longitudinal cross-sectional view of an embodiment of a hair styling device according to the present invention comprising a delivery means and a means to further align and hold with teeth wherein a button has been actuated.
Figure 20D:
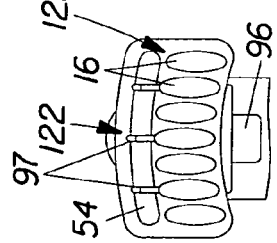
FIG. 20D is a front elevational view of an embodiment of a hair styling device according to present invention comprising a bundling means, an air outlet, and a button.

FIGS. 18A, 18B and 18C depicts a non-limiting exemplary embodiment of a hair styling device of the present invention. FIGS. 18A, 18B and 18C depicts in this embodiment an additional applicator means (124) to deliver a styling composition (31). The additional applicator means (124) may comprise a tube (86) and a rod (82). A tube (86) may comprise plural outlet (42) on side of tube (86). A rod (82) is positioned inside of a tube (86). A rod (82) may comprise a ditch (83) on both sides of tube (86). The ditch (83) is positioned inside of plural outlet (42) for styling composition (31). A route of styling composition (31) is made by the ditch (83) and the wall of tube (86) and goes out from plural outlet (42). A styling composition (31) that is pushed out by a pump (27) travels through ditch (83) and travels out from plural outlets (42). When the applicator means (4) is comprised of only capillary tube (28), it may be difficult that a styling composition (31) is delivered at uniform quantity and uniform pressure from each plural outlet (42), because the plural outlet (42) are set on side of tube (86) and are more than one in number. When the applicator means (4) is comprised of a tube (86) and a rod (82), one route of a styling composition (31) is comprised of the same structure as capillary tube (28) that has plural outlets (42) on one side. In this embodiment a styling composition (31) may be delivered at a uniform quantity and uniform pressure as plural outlets (42) are set on one side. In this embodiment, a hair styling device comprising a tube (86) and a rod (82) may have similar performance when compared a hair styling device comprising two capillary tubes (28) which may comprise plural outlets (42) at one side and wherein this embodiment may be more compact than the embodiment comprising two capillary tubes (28).

FIGS. 19A, 19B, 19C, 20A, 20B, 20C, 20D and 21A, 21B, 21C, and 21D depict non-limiting exemplary embodiment of a hair styling device of the present invention. FIGS. 19A, 19B, 19C, 20A, 20B, 20C, 20D and 21A, 21B, 21C, and 21D depict an embodiment comprising a second (91). A pump (92) and third inlet (93) may be connected with a reservoir (94). The reservoir (94) may be comprised of a flexible film or a laminate. The flexible film may be any conventional known film or laminate. In a particular embodiment of the present invention the flexible film may be an aluminum film or a plastic film. The reservoir (94) may be comprised of a styling composition (31) inside. In one embodiment there is no air present in the reservoir (94). When a button (96) is pushed, a pump (92) is moved. When pump (92) is moved, pump (92) draws styling composition (31) from the reservoir (94) and sends the styling composition (31) into a tube assembly (100). When the pump (92) draws the styling composition (31), a quantity of styling composition (31) in reservoir (94) is lost and the reservoir (94) shrinks, as there is no air present in the reservoir (94). In the present embodiment, pump (92) and third inlet (93) are constantly soaked in a styling composition (31). If second device (91) is used or operated at any orientation, second device (91) may supply a styling composition (31) to the hair strands (15). When button (96) is pushed, a lift plate (97) may be raised up by a second lever (98) which is connected to a button (96). The lift plate (97) may raise up, remaining parallel to the tines (16). The lift plate (97) may comprise a tooth (99). The hair strands (15) is lifted by a lift plate (97) as tooth (99) of lift plate (97) catches hair strands (15). The height of the hair strands (15) may be equal at any position of the tines (16), as the lift plate (97) remains parallel to the tines (16). In the present embodiment, where the tines (16) are in combination with the lift plate (97), the tines (16) may provide guide to a movement of the lift plate (97). The tines (16) remains in contact with a scalp (19), as the lift plate (97) raises. As the lift plate (97) raises, the widths of a bundle of hair strands (15) remain constant, and remain at effective size for providing lift to the hair strands (15), as the tines (16) remain in contact with the scalp (19).

FIGS. 21A, 21B, 21C, 21D and 22A and 22B depicts a non-limiting exemplary embodiment of a hair styling device of the present invention. FIGS. 21A, 21B, 21C, 21D and 22A and 22B depict a further embodiment of the present invention comprising a tube assembly (100). A ditch (101) of a rod (102) branches at a certain position. A styling composition (31) that is sent by a pump (92) goes to plural outlets (42) of a tube (86) through a ditch (101). Each length of a ditch (101) from a fourth inlet (103) of a tube assembly (100) to each plural outlet (42) is equal. A styling composition (31) is pushed out at the equal pressure from each plural outlet (42), as each length of a ditch (101) from a fourth inlet (103) of a tube assembly (100) to each plural outlet (42) is equal. Styling composition (31) is supplied from each plural outlet (42) in a uniform manner, as the styling composition (31) is pushed out at equal pressure from each of the plural outlet (42). In this embodiment, the applicator means (124) may comprise a rod (102) and a tube (86). A driving means (123) that transport the styling composition (31) may comprise a tube assembly (100) and a pump (92). A means to set (125) that dries the styling composition (31) and sets hair strands (15) comprises a dryer (4) and a tine assembly (104).

FIGS. 23A, 23B, 23C and 23D depicts a non-limiting exemplary embodiment of a hair styling device of the present invention. FIGS. 23A, 23B, 23C and 23D depict a further embodiment of the present invention comprising a second lever (126), a shutter (127), a heat plate (128), a pump (129) and a reservoir (130). A second lever (126) can begin the process of styling hair by being actuated. The second lever (126), when actuated, can regulate the opening or closing of a shutter (127). Further, the second lever (126), when actuated, may activate a pump (129). The second lever (126), when actuated, may move a heat plate (128) to pinch. A shutter (127) may close ports (131) which may be located on both sides of a capillary tube (132) to prevent drying of a styling composition. All of the ports (131) may be open when the second lever (126) is actuated. When the second lever (126) is not actuated, the shutter (127) may close ports (131) and when the ports (131) are closed there is no chance for styling composition to be exposed to the air and styling composition will neither be dried nor clogged the ports (131). In a further embodiment, the ports (131) may be made by a neoprene rubber or flexible material and may be easily deformed to unclog or break-up possible styling composition build-up when the shutter (127) closes and opens across the ports (131). The flexible material may be made of any known conventional flexible material such as polyolefins or rubber. A shutter (127) may hold the hair which is pushed by a heat plate (128) from the opposite side. A heat plate (128) may come in contact with the hair and dry the styling composition. The styling composition will set in a range of about 1 seconds to about 20 seconds. The heat plate (128) may be located inside of tines (133) and may contact hair inserted between tines (133) when the second lever (126) is actuated. In an embodiment of the present invention, a means to hold and further align (122) may be comprised of a heat plate (128). The action of holding and further aligning the hair may be achieved by a heat plate (128) which may be displaced horizontally or in parallel displacement with the scalp. A pump (129) is connected to a second lever (126). The pump (129) may deliver the styling composition from a reservoir (130) to the ports and generate a pressure to deliver the styling composition from the port to the hair. The pump (129) may supply an appropriate amount of styling composition when the second lever (126) is actuated. When the second lever (126) is actuated, the shutter (127) moves to open the ports (131). A pump (129) may deliver the styling composition from a reservoir (130) to each port (131). When the second lever is released, the shutter (127) may move in the opposite direction to close each port (131) and the heat plates (128) release the hair. A reservoir (130) may comprise the styling composition. An enclosure of the reservoir (130) may be transformed not to generate a negative pressure by delivering styling composition out. Only styling composition may be stored in the reservoir (130). A pump (129) and a reservoir (130) may have be specific to only connect to each other and thereby cannot accept the refill of styling juice or any other chemical material. In this embodiment, a means to set that dries the styling composition and sets hair strands comprises a heat plate (128). The heat plate delivers heat in a temperature range of from about 100° C. to about 180 C. A delivery system may be comprised of a reservoir (130) and a pump (129). Further, a driving means that transport the styling composition may comprise a pump (129). And further, a bundling means (121) may be comprised of a tines (133).

Styling Composition

The components, including those which may optionally be added, of the actives and compositions used in the present invention, as well as methods for preparation, and methods for use, are described in detail below. A styling composition of the present invention may be comprised of a material that can hold hair together. The styling composition component of the present invention may include any of the following materials mentioned and described in below, either alone or in combination.

Any fixing polymer known to provide a styling benefit can be used. In particular, fixing polymers selected from anionic, cationic, amphoteric and nonionic polymers and mixtures thereof can be used. The fixing polymers may be used in solubilized form or in the form of dispersions of solid polymer particles.

Cationic Polymers

The cationic fixing polymers which can be used according to the present invention are preferably selected from polymers containing primary, secondary, tertiary and/or quaternary amine groups forming part of the polymer chain or directly connected thereto, and having a weight-average molecular weight of from 500 to about 5,000,000 preferably from 1000 to 3,000,000 and more preferably 10,000 to 1,000,000.

Polymers of interest for the current application are:

(1) homopolymers or copolymers derived from acrylic or methacrylic esters or amides and containing at least one of the following units:

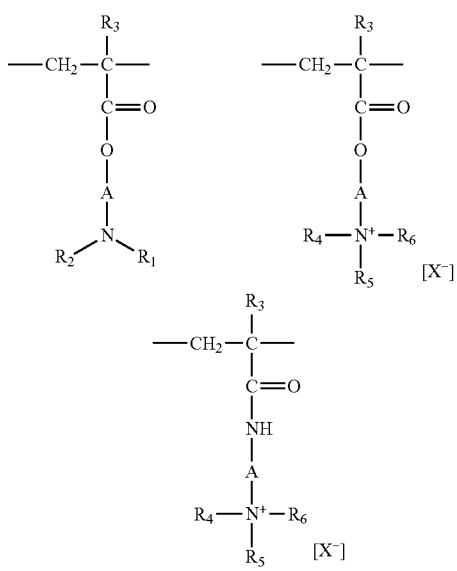

wherein:
- $R_3$ denotes a hydrogen atom or a $CH_3$ radical;
- A is a linear or branched alkyl group of 1 to 6 carbon atoms or a hydroxyalkyl group of 1 to 4 carbon atoms;
- $R_4$, $R_5$ and $R_6$, which are identical or different, represent an alkyl group having from 1 to 18 carbon atoms or a benzyl radical;
- $R_1$ and $R_2$, which are identical or different, represent hydrogen or an alkyl group having from 1 to 6 carbon atoms;
- X denotes a methosulphate anion or a halide such as chloride or bromide;
- The copolymers of family (1) also contain one or more monomer units which may be selected from the family of acrylamides, methacrylamides, diacetone acrylamides, acrylamides and methacrylamides substituted on the nitrogen with $C^1$-$C^6$ lower alkyls, acrylic or methacrylic acids or esters thereof, vinyllactams such as vinylpyrrolidone or vinylcaprolactam, and vinyl esters. Some prefer polymers under the group #1 are: quaternized or non-quaternized vinylpyrrolidone/dialkylaminoalkyl acrylate or methacrylate copolymers, such as GAFQUAT 734, GAFQUAT 755, COPOLYMER 845, 958 and 937 from ISP; dimethylaminoethyl; methacrylate/-vinylcaprolactam/vinylpyrrolidone terpolymers such as GAFFIX VC 713 and ACP-1018 from ISP; and quaternized vinylpyrrolidone/dimethylaminopropyl methacrylamide copolymer, such as GAFQUAT HS 100 from ISP.
- (2) quaternized polysaccharides like celluloses, preferably chosen from cellulose derivatives grafted with a water-soluble monomer in the form of quaternary ammonium, in particular, hydroxyalkylcelluloses such as hydoxymethyl-, hydoxyethyl- and hydroxypropyl-celluloses grafted with a salt of methacryloyl-ethyltrimethyl ammonium, methacrylamidopropyltrimethyl ammonium, or dimethyldiallyl ammonium. They can be obtained as "Celquat L 200" and "Celquat H 100" by the National Starch. They are also known as Polyguaternium 4. When the cationic polysaccharide is a cellulose ether containing hydroxyethylcelluloses having reacted with an epoxy substituted by a trimethyl ammonium group, they are available as "JR 400," "JR 125," "JR 30M", "LR 400" and "LR 30M" by Amerchol.
- (3) quaternized copolymers of vinylpyrrolidone/dialkylaminoalkyl acrylate or methacrylate, quaternized copolymer of vinyl pyrrolidone/dialkylaminoalkyl acrylamide or methacrylamide such as Polyquaternium 11 and of quaternized copolymer of vinylimidazole;
- (4) chitosans or salts thereof, in particular, chitosan acetate, lactate, glutamate, gluconate or pyrrolidonecarboxylate.

Anionic Polymers

The anionic fixing polymers preferably used are polymers containing groups derived from carboxylic, sulphonic or phosphoric acid and have a weight-average molecular weight of approximately from 500 to 5,000,000, preferably from 1000 to 3,000,000 and more preferably 10,000 to 1,000,000.

I. The carboxylic groups are provided by unsaturated mono- or dicarboxylic acid monomers such as those corresponding to the formula (A1):

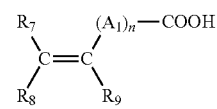

in which n is an integer from 0 to 10,
$A_1$ denotes a methylene group, optionally linked to the carbon atom of the unsaturated group or to the neighboring methylene group when n is greater than 1 via a hetero atom such as oxygen or sulphur,
$R_7$ denotes a hydrogen atom, or a phenyl or benzyl group,
$R_8$ denotes a hydrogen atom or a $C_1$-$C_6$ lower alkyl or carboxyl group and
$R_9$ denotes a hydrogen atom, a $C_1$-$C_6$ lower alkyl group or a —$CH_2$—COOH, phenyl or benzyl group.

Lower alkyl radical preferably means a group having 1 to 6 carbon atoms and in particular methyl and ethyl.

Preferred anionic fixing polymers containing carboxylic groups are: homo- or copolymers of acrylic or methacrylic acid or salts such as ULTRAHOLD by BASF and also the copolymers of acrylic acid and acrylamide and/or polyhydroxycarboxylic acids; copolymers of acrylic or methacrylic acids with a monoethylenic monomer such as ethylene, styrene, vinyl esters, esters of acrylic or methacrylic acid. Mention may also preferably be made of the copolymers of acrylic acid and of $C_1$-$C_4$ alkyl methacrylate and terpolymers of vinylpyrrolidone, of acrylic acid and of $C_1$-$C_{20}$ alkyl methacrylate, for example of lauryl methacrylate, such as ACRYLIDONE LM by ISP and methacrylic acid/ethyl acrylate/tert-butyl acrylate terpolymers such LUVIMER IOOP by BASF; copolymers derived from crotonic acid, such as the resins 28-29-30-26-13-14 and 28-13-10 sold by the company National Starch and vinyl acetate/crotonic acid (90/10) copolymer sold by BASF under the name "LUVISET CA 66; copolymers derived from $C_4$-$C_8$ mono-unsaturated carboxylic acids or anhydrides; and polyacrylamides containing carboxylate groups.

II. The polymers comprising sulphonic groups are polymers containing vinylsulphonic, styrenesulphonic, naphthalenesulphonic or acrylamidoalkylsulphonic units. These polymers may preferably be selected from: polyvinylsulphonic acid salts having a weight-average molecular weight of approximately from 1000 to 100,000, as well as copolymers with an unsaturated comonomer such as acrylic or methacrylic acids and esters thereof, as well as acrylamide or derivatives thereof, vinyl ethers and vinylpyrrolidone; polystyrenesulphonic acid salts, the sodium salts having a weight-average molecular weight of about 500,000 and of about 100,000 such as FLEXAN 500 and FLEXAN 130 by National Starch; and polyacrylamidesulphonic acid salts, and more particularly polyacrylamidoethylpropanesulphonic acid The anionic fixing polymers are preferably selected from acrylic acid copolymers such as the acrylic acid/ethyl acrylate/N-tert-butylacrylamide terpolymer sold under the name ULTRAHOLD STRONG by BASF, copolymers derived from crotonic acid such as vinyl acetate/vinyl tert-butylbenzoate/crotonic acid terpolymers and crotonic acid/vinyl acetate/vinyl neododecanoate terpolymers sold under the name RESIN 28-29-30 by National Starch.

Amphoteric Polymers

The amphoteric fixing polymers may be selected from polymers containing units A and B randomly distributed in the polymer chain, where A denotes a unit derived from a monomer containing at least one basic nitrogen atom and B denotes a unit derived from an acidic monomer containing one or more carboxylic or sulphonic groups, or alternatively A and B can denote groups derived from zwitterionic monomers of carboxybetaines or of sulphobetaines. The amphoteric fixing polymers more particularly preferred corresponding to the definition given above are selected from the following polymers:
 (1) Polymers resulting from the copolymerization of a monomer derived from a vinyl compound bearing a carboxylic group such as, more particularly, acrylic acid, methacrylic acid, maleic acid or .alpha.-chloroacrylic acid and of a basic monomer derived from a substituted vinyl compound containing at least one basic atom such as, more particularly, dialkylaminoalkyl methacrylate and acrylate, dialkylaminoalkylmethacrylamide and acrylamide.
 (2) Polymers containing units derived from:
  (a) at least one monomer selected from acrylamides or methacrylamides substituted on the nitrogen with an alkyl radical. The N-substituted acrylamides or methacrylamides more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide and N-dodecylacrylamide as well as the corresponding methacrylamides.
  (b) at least one acidic comonomer containing one or more reactive carboxylic groups. The acidic comonomers are more preferably selected from acrylic, methacrylic, crotonic, itaconic, maleic and fumaric acids as well as the alkyl monoesters having 1 to 4 carbon atoms of maleic or fumaric acids or anhydrides.
  (c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate. The preferred basic comonomers are aminoethyl, butylaminoethyl, N—N'-dimethylaminoethyl or N-tert-butylaminoethyl methacrylates.
 A copolymers representing this type is octylacrylamide/acrylates/butylaminoethyl methacrylate copolymer, such as the products sold under the name AMPHOMER or LOVOCRYL 47 by the company National Starch.
 (3) Polymers containing zwitterionic units of formula (AM4):

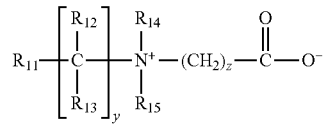

in which $R_{11}$, denotes a polymerizable unsaturated group such as an acrylate, methacrylate, acrylamide or methacrylamide group, y and z represent an integer from 1 to 3, $R_{12}$ and $R_{13}$, which are identical or different, represent a hydrogen atom, methyl, ethyl or propyl and $R_{14}$ and $R_{15}$, which are identical or different, represent a hydrogen atom or an alkyl radical such that the sum of the carbon atoms in $R_{14}$ and $R_{15}$ does not exceed 10.
  The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate.
  By way of example, mention may preferably be made of the copolymer of methyl methacrylate/methyl dimethylcarboxymethylammonioethylmethacrylate such as DIAFORMER Z301 by the company Clariant.
 (4) Chitosan-derived polymers and polymers derived from the N-carboxyalkylation of chitosan, such as N-carboxy-methyl chitosan or N-carboxybutyl chitosan.
 (5) Copolymers of $(C_1-C_5)$alkyl vinyl ether/maleic anhydride partially modified by semiamidation with an N,N-dialkylaminoalkylamine such as N,N-dimethylaminopropylamine or by semiesterification with an N,N-dialkanolamine. These copolymers may also contain other vinyl monomers such as vinylcaprolactam.

The amphoteric fixing polymers particularly preferred according to the invention are those of family (3), such as the copolymers whose CTFA name is octylacrylamide/acrylates/butylaminoethyl methacrylate copolymer such as AMPHOMER, AMPHOMER LV 71 or LOVOCRYL 47 National Starch and those of family (4) such as the copolymer of methyl methacrylate/methyl dimethylcarboxymethylammonioethylmethacrylate, DIAFORMER Z301 by Clariant.

Nonionic Polymers

The nonionic fixing polymers are selected from:
 vinyl acetate homopolymers;
 copolymers of vinyl acetate and of acrylic ester, such as RHODOPAS AD 310 by Rhone-Poulenc;
 copolymers of vinyl acetate and of maleic ester such APPRETAN MB EXTRA by Hoechst;
 polyvinyl chloride homopolymers;
 copolymers of polyethylene and of maleic anhydride;
 polyurethanes
 homopolymers of polyvinyl pyrridoline (PVP)
 copolymers of PVP and of vinyl acetate such as LUVISKOL VA 64 Powder by BASF.
 Hydroxyalkylcellulose Mention may be made, for example, of: hydroxyethylcellulose, the cellulose ethers generally used in cosmetics, guar gums, carob gums.

The alkyl radicals of the nonionic polymers have from 1 to 6 carbon atoms except where otherwise mentioned.

Polymers of Grafted Silicone Type

It is also possible to use fixing polymers of grafted silicone type comprising a polysiloxane portion and a portion consisting of a non-silicone organic chain, one of the two portions constituting the main chain of the polymer, the other being grafted onto the said main chain. These polymers are preferably anionic.

Such polymers are, for example copolymers which can be obtained by radical polymerization starting with a monomer mixture consisting of:

(a) 50 to 90% by weight of tert-butyl acrylate;
(b) 0 to 40% by weight of acrylic acid;
(c) 5 to 40% by weight of silicone macromer of formula:

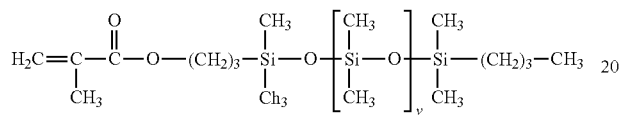

with v being a number ranging from 5 to 700; the weight percentages being calculated relative to the total weight of the monomers.

Level

The fixing polymer or polymers are present, for example, in concentrations of from 0.1% to 20% by weight, and preferably in concentrations of from 0.5% to 10% by weight, and more preferably 1% to 5% by weight of the composition.

Volatile Carriers

In the present invention, a liquid carrier may help to solubilize or disperse the styling compositions described hereinbefore. The liquid carrier can comprise one or more liquid carriers provided that the selected styling composition is sufficiently miscible/dispersible in the selected liquid carrier.

The total concentration of the liquid carrier in the composition will vary with the type of liquid carrier selected, the type of styling composition used in combination with the liquid carrier, and the solubility of the selected styling composition in the selected liquid carrier, and so forth. Preferred total concentration of the liquid carrier ranges from about 80% to about 99.9%, preferably from about 90% to about 99.5%, more preferably from about 95% to about 99%, by weight of the composition.

Suitable liquid carriers for use in the compositions of the present invention are volatile liquid carrier materials. In this context, the term "volatile" refers to materials which have a boiling point of less than about 260° C., preferably from about 50° C. to about 260° C., more preferably from about 60° C. to about 150° C. (at about one atmosphere of pressure).

Nonlimiting examples of volatile liquid carriers include water, organic solvents such as $C_1$-$C_6$ alkanols, and combinations thereof. Specific examples of suitable $C_1$-$C_6$ alkanols include, but are not limited to, ethanol, n-propanol, isopropanol, n-butanol, amyl alcohol, and mixtures thereof. Preferred $C_1$-$C_6$ alkanols include $C_2$-$C_4$ monohydric alcohols such as ethanol, isopropanol, and mixtures thereof. Water is the preferred volatile liquid carrier.

Neutralization

The anionic or amphoteric fixing polymers may, if necessary, be partially or totally neutralized. The neutralizing agents are, for example, sodium hydroxide, potassium hydroxide, 2-amino-2-methyl-1-propanol, monoethanolamine, triethanolamine or triisopropanolamine, and inorganic or organic acids such as hydrochloric acid or citric acid.

Plasticizer

The compositions according to the invention can include at least one plasticizing agent in order to improve the mechanical properties and the adhesion to hair of the deposited film-forming polymer after application and drying. Some plasticizing agents which may be used according to the invention, are:

diethylene glycol ethyl ether, diethylene glycol methyl ether, diethylene glycol butyl ether, diethylene glycol hexyl ether ethylene glycol ethyl ether, ethylene glycol butyl ether, ethylene glycol hexyl ether, propylene glycol derivatives and in particular propylene glycol phenyl ether, propylene glycol diacetate, dipropylene glycol butyl ether or tripropylene glycol butyl ether propylene glycol methyl ether, dipropylene glycol methyl ether and tripropylene glycol methyl ether.

1,3-butylene glycol diethyl, dibutyl and diisopropyl phthalates and adipates diethyl and dibutyl tartrates diethyl, dibutyl and di(2-ethylhexyl) phosphates glycerol esters, such as glyceryl diacetate (diacetin) and glyceryl triacetate (triacetin).

The at least one plasticizing agent is more preferably selected from those which are hydrophilic or water-soluble. The at least one plasticizing agent is present in a proportion preferentially ranging from 0 to 20% by weight, relative to the weight of the film-forming polymer In a further embodiment of the present invention, a composition of matter for use in a hair care operation, comprises a fixing polymer and a carrier, the composition being releasably held within a reservoir, the reservoir comprising fluid-impermeable walls, the walls having an attachment means associated therewith for removably attaching the reservoir to a hair styling device, the reservoir having a means for providing the composition onto the hair wherein the reservoir is in fluid communication with the hair styling device.

Optional Components

In addition to the components described above, the compositions of the present invention may further comprise one or more optional components known or otherwise effective for use in hair care or personal care products, provided that the optional components are physically and chemically compatible with the components described above, or do not otherwise unduly impair product stability, aesthetics or performance. Nonlimiting examples of such optional components are disclosed in *International Cosmetic Ingredient Dictionary*, Fifth Edition, 1993, and CTFA *Cosmetic Ingredient Handbook*, Second Edition, 1992, both of which are incorporated by reference herein in their entirety.

The compositions of the invention can contain adjuvants that are common in the cosmetics field, such as emulsifiers; surfactants; conditioning actives (moisturizers; emollients); sunscreens; anti-free-radical agents; sequestering agents; antioxidants; preserving agents; acidifying or basifying agents; fragrances; dyestuffs; modified or non-modified, non-volatile silicones; reducing agents. The amounts of these various adjuvants are those used conventionally in the fields considered.

The present invention may, in some embodiments, further comprise additional optional components known or otherwise effective for use in hair care or personal care products. The concentration of such optional ingredients generally ranges from zero to about 25%, more typically from about 0.05% to about 25%, even more typically from about 0.1% to about 15%, by weight of the composition. Such optional components should also be physically and chemically compatible with the essential components described herein, and should not otherwise unduly impair product stability, aesthetics or performance.

Methods of Manufacture

The compositions of the present invention may be prepared by any known or otherwise effective technique, suitable for providing a composition provided that the resulting composition provides the excellent styling benefits described herein. Methods for preparing the embodiments of the present invention include conventional formulation and mixing techniques.

The hair styling device of the present invention may be prepared by any known or otherwise effective technique, suitable for providing a device that provides the excellent styling benefits described herein. Methods for preparing the embodiments of the present invention include conventional manufacture techniques. As a further embodiment of the present invention, materials which may be used in the manufacturing process of the hair styling device include, but are not limited to: PET: heat-resistant plastic, PET may be used for example in an external housing; PC: heat-resistant plastic and transparent plastic, PC may be used for example in a reservoir case; PPS: heat-resistant plastic and chemical-resistant plastic, PPS may be used for example in a chamber case; and ABS: shock-resistant plastic, ABS may be used for example in external parts of a device. As may be known in the art, with regard to heat-resistance, PPS has the highest heat resistance for plastic and the subsequent order would be PPS>PET>PC>ABS. The embodiments of the present invention may use the appropriate and suitable plastic as needed.

Non-limiting exemplary embodiments of the hair styling device of the present invention may comprise a hair styling device that may be from about 150 mm to about 400 mm in length and from about 10 mm to about 80 mm in height per gripping means and about 20 mm to about 100 mm in width.

Methods of Use

The present invention comprises a method of providing lift and volume to a mass of undifferentiated hair stands on a scalp region wherein hair to be lifted is passed through a bundling means which may gather hair strands into hair bundles; wherein a delivery system, in fluid communication with the bundling means, may provide a styling composition to the hair strands; and a means to set may provide an air source or a heat plate in order to set the styling composition. The air source delivers air in a temperature range of about 25° C. to about 140° C.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified concentrations are weight percents, unless otherwise specified.

Examples

| | Example I | Example II | Example III | Example IV | Example V |
|---|---|---|---|---|---|
| Water | Q.S. | Q.S. | Q.S. | Q.S. | Q.S. |
| PVP/VA (1) | 1.0 | 1.0 | — | — | 1.0 |
| Polyurethane-1 (2) | — | — | 3.0 | — | — |
| Polyvinylcaprolactam (3) | — | 1.0 | — | 2.0 | — |
| Hexymethicone (4) | — | — | 3.0 | — | — |
| Isosteareth-20 | 0.65 | — | 0.3 | — | 0.5 |
| Undeceth-9 | — | 0.3 | 0.3 | 0.4 | — |
| Benzyl Alcohol | 0.5 | 0.5 | 0.5 | 0.5 | 0.5 |
| Phenoxyethanol | 0.3 | 0.3 | 0.3 | 0.3 | 0.3 |
| Methyl Paraben | 0.2 | 0.2 | 0.2 | — | 0.2 |
| Disodium EDTA | 0.12 | 0.12 | 0.12 | 0.12 | 0.12 |
| Perfume | 0.2 | 0.1 | 0.2 | 0.1 | 0.1 |

(1) Luviscol VA 73W (50% active) from BASF
(2) Luviset PUR (30% active) from BASF
(3) Luvitec VCAP (30% active) from BASF
(4) Silcare 41M10 from Archimica

| | Example VI | Example VII | Example VIII | Example IX | Example X |
|---|---|---|---|---|---|
| Water | Q.S. | Q.S. | Q.S. | Q.S. | Q.S. |
| PVP (1) | 1.5 | 2.0 | — | 0.5 | 0.5 |
| Polyvinylcaprolactam (2) | 0.5 | — | 1.2 | — | — |
| Chitosan | — | 0.7 | 0.3 | — | 0.5 |
| Lactic Acid | — | 0.7 | 0.7 | 0.7 | 0.7 |
| PEG-40 Hydrogenated Castor Oil | 0.2 | 0.4 | 0.4 | — | 0.2 |
| Polysorbate 20 (3) | 0.3 | 0.4 | 0.6 | 0.6 | 0.2 |
| DMDM Hydantoin (4) | 0.5 | 0.5 | 0.5 | 0.5 | 0.5 |
| PEG-60 Almond Glycerides | — | 0.2 | 0.1 | — | 0.3 |
| Polysorbate 80 (5) | 0.3 | 0.2 | — | — | 0.4 |
| Fragance | .1 | 0.1 | 0.1 | 0.1 | 0.1 |
| Iodopropynyl Butylcarbamate | 0.5 | 0.5 | 0.5 | 0.5 | 0.5 |
| Panthenol | — | 0.01 | 0.05 | — | 0.05 |
| Ethylhexyl Salicylate | — | 0.01 | — | 0.05 | 0.1 |
| Panthenyl Ethyl Ether | — | 0.01 | 0.05 | — | 0.05 |

(1) CAS# 9003-39-8
(2) Luvitec VCAP (30% active) from BASF
(3) CAS# 9005-64-6
(4) CAS# 6440-58-0
(5) CAS# 9005-65-6

For examples XI to XV, mix component of main mix until they are well dispersed. In a separate vessel, mix components of the premix. Add premix to main mix.

| | Example XI | Example XII | Example XIII | Example XIV | Example XV |
|---|---|---|---|---|---|
| Premix | | | | | |
| Copolymer I | 0.25 | — | — | 0.5 | 0.5 |
| Copolymer II | — | 0.5 | 1.0 | — | — |
| Dimethylstearamine (1) | 0.21 | — | — | 0.2 | — |
| Dimethylmyristamine (2) | — | 0.33 | 0.67 | 0.17 | 0.13 |
| Cyclopentasiloxane (3) | 2.0 | — | — | 4.0 | — |
| Hexymethicone (4) | — | — | 3.0 | — | — |
| Hexamethyl Disiloxane | 2.0 | — | — | — | — |
| Isodedecane | — | 5.0 | 7.0 | — | 5.0 |
| Main Mix | | | | | |
| Water | Q.S. | Q.S. | Q.S. | Q.S. | Q.S. |
| PEG-8 (5) | — | — | — | 0.5 | — |
| Silicone Emulsion (6) | — | 0.4 | — | — | == |

-continued

| | | | | | |
|---|---|---|---|---|---|
| Isosteareth-20 | — | 0.45 | 0.3 | — | 0.2 |
| Undeceth-9 | 0.3 | — | 0.2 | 0.4 | 0.2 |
| Benzyl Alcohol | 0.5 | 0.5 | 0.5 | 0.5 | 0.5 |
| Phenoxyethanol | 0.3 | — | — | 0.3 | 0.3 |
| Methyl Paraben | 0.2 | 0.2 | 0.2 | — | — |
| Disodium EDTA | 0.12 | 0.12 | 0.12 | 0.12 | 0.12 |
| Perfume | 0.1 | 0.1 | 0.1 | 0.1 | 0.1 |

Copolymer I: Poly[t-butyl acrylate/acrylic acid/polydimethylsiloxane macromonomer] 60/20/20
Copolymer II: Poly [t-butyl acrylate/methacrylic acid/polydimethylsiloxane macromonomer] 70/10/20
(1) Armeen DM18D from Akzo
(2) Armeen DM14D from Akzo
(3) SF1202 from GE
(4) Silcare 41M10 from Archimica
(5) Carbowax 400 from Union Carbide
(6) 50% dimethicone emulsion from Toray Silicones

| | Example XVI | Example XVII | Example XVIII |
|---|---|---|---|
| Water | Q.S. | Q.S. | Q.S. |
| Ethanol, Denatured | 10.0 | 10.0 | 15.0 |
| PVP/VA (1) | 0.5 | — | 1.0 |
| Polyurethane-1 (2) | — | — | 1.0 |
| Polyvinylcaprolactam (3) | — | 2.0 | — |
| PEG-8 (4) | — | 0.5 | — |
| diisopropyl phthalate | — | — | 0.1 |
| Cyclopentasiloxane (5) | 2.0 | 2.0 | — |
| Isosteareth-20 | 0.1 | 0.2 | — |
| Perfume | 0.1 | 0.2 | 0.1 |

(1) Luviscol VA 73W (50% active) from BASF
(2) Luviset PUR (30% active) from BASF
(3) Luvitec VCAP (30% active) from BASF
(4) Carbowax 400 from Union Carbide
(5) SF1202 from GE The compositions illustrated in Examples I to XVIII illustrate specific embodiments of the present invention, but are not intended to be limiting thereof.

All exemplified compositions can be prepared by conventional formulation and mixing techniques. Component amounts are listed as weight percents and exclude minor materials such as diluents, filler, and so forth. The listed formulations, therefore, comprise the listed components and any minor materials associated with such components.

Having shown and described various embodiments of the present invention, further adaptations of the present invention as described herein can be accomplished by appropriate modifications by one of ordinary skill in the art without departing from the scope of the present invention. Several of these potential modifications and alternatives have been mentioned, and others will be apparent to those skilled in the art. For example, while exemplary embodiments of the inventive system have been discussed for illustrative purposes, it should be understood that the elements described may be constantly updated and improved by technological advances. Accordingly, the scope of the present invention should be considered in terms of the following claims and is understood not to be limited to the details of structure, operation or process steps as shown and described in the specification and drawings.

What is claimed is:

1. A hair styling device capable of providing lift to a mass of undifferentiated hair stands on a scalp region comprising:
   a) tines for gathering hair strands into hair bundles wherein the tines are capable of touching the scalp
   b) a reservoir, in fluid communication with the tines, comprising a styling composition comprising a fixing polymer; and
   c) a means to hold and further align the hair strands along and beyond the tines a greater distance from the scalp region than the tines for gathering hair strands into hair bundles distance from the scalp region;
   d) an applicator means, in fluid communication with the reservoir, for applying the styling composition wherein the applicator means is located inside or along the tines which are capable of touching the scalp.

2. A hair styling device according to claim 1 wherein the hair styling device further comprises a means to set the styling composition.

3. A hair styling device according to claim 2 wherein the means to set the styling composition is selected from the group consisting of an air source, a heat plate or mixtures thereof.

4. A hair styling device according to claim 3 wherein the means to set the styling composition is an air source.

5. A hair styling device according to claim 3 wherein the means to set the styling composition is a heat plate.

6. A hair styling device according to claim 4 wherein the air source delivers air in a temperature range of about 25° C. to about 140° C.

7. A hair styling device according to claim 5 wherein the heat plate delivers heat in a temperature range of from about 100° C. to about 180 C.

8. A hair styling device according to claim 2 wherein the means to hold and further align the hair strands is located above the tines.

9. A hair styling device according to claim 2 wherein the means to hold and further align the hair strands provides alignment of the hair bundles capable of being substantially orthogonal to a scalp region.

10. A hair styling device according to claim 2 wherein the means to hold the hair strands is displaced from about 0 to about 10 mm from the tines.

11. A hair styling device according to claim 2 wherein the tines is hollow.

12. A hair styling device according to claim 2 wherein the applicator means is a capillary tube.

13. A hair styling device according to claim 2 wherein the styling composition is capable of being delivered to a proximal end of the hair bundles at about 1 mm to about 20 mm distance from the scalp region.

14. A hair styling device according to claim 2 wherein the styling composition will set in a range of about 1 seconds to about 20 seconds.

15. A hair styling device according to claim 2 wherein the reservoir is a pre-filled delivery system which is replaceable.

16. A hair styling device according to claim 2 wherein the reservoir can be filled with the styling composition.

17. A hair styling device according to claim 1 wherein the tines are about 20 mm in height.

18. A hair styling device according to claim 1 wherein the tines are from about 85 mm to about 90 mm in length.

19. A hair styling device according to claim 1 wherein the tines are from about 5 mm to about 10 mm in width.

20. A hair styling device according to claim 1 wherein the tines are from about 1.0 mm to about 2.5 mm distance apart.

21. A hair styling device capable of providing lift to a mass of undifferentiated hair stands on a scalp region comprising:
   (a) tines for gathering hair strands into hair bundles, and the hair strands bundle is made between adjacent tines and at a height of the tines;
   (b) a reservoir, in fluid communication with a bundling means, comprising a styling composition; and (c) a means to hold and further align the hair strands along and beyond the tines;
(d) a capillary tube, in fluid communication with the reservoir, capable of applying the styling composition to the hair strands and said capillary tube being set inside of tines or being set parallel to tines;

and wherein the styling composition is capable of being supplied to roots of the hair strands.

* * * * *